(12) United States Patent
Yamashita et al.

(10) Patent No.: US 12,053,366 B2
(45) Date of Patent: Aug. 6, 2024

(54) CYLINDRICAL STRUCTURE

(71) Applicant: Toray Industries, Inc., Tokyo (JP)

(72) Inventors: Kyohei Yamashita, Otsu (JP); Koji Kadowaki, Otsu (JP); Kazuhiro Tanahashi, Otsu (JP); Nobuaki Tanaka, Otsu (JP); Satoshi Yamada, Otsu (JP); Hiroshi Tsuchikura, Otsu (JP)

(73) Assignee: Toray Industries, Inc., Tokyo (JP)

( * ) Notice: Subject to any disclaimer, the term of this patent is extended or adjusted under 35 U.S.C. 154(b) by 1351 days.

(21) Appl. No.: 16/497,745

(22) PCT Filed: Mar. 30, 2018

(86) PCT No.: PCT/JP2018/013681
§ 371 (c)(1),
(2) Date: Sep. 25, 2019

(87) PCT Pub. No.: WO2018/181918
PCT Pub. Date: Oct. 4, 2018

(65) Prior Publication Data
US 2020/0022799 A1 Jan. 23, 2020

(30) Foreign Application Priority Data
Mar. 31, 2017 (JP) .................. 2017-070163

(51) Int. Cl.
| | |
|---|---|
| A61F 2/06 | (2013.01) |
| A61L 27/16 | (2006.01) |
| A61L 27/18 | (2006.01) |
| A61L 27/34 | (2006.01) |
| A61L 27/50 | (2006.01) |
| A61L 29/04 | (2006.01) |
| A61L 29/08 | (2006.01) |
| A61M 1/36 | (2006.01) |
| D03D 3/02 | (2006.01) |
| D03D 13/00 | (2006.01) |
| F16L 58/10 | (2006.01) |

(52) U.S. Cl.
CPC ............. *A61F 2/06* (2013.01); *A61L 27/16* (2013.01); *A61L 27/50* (2013.01); *A61L 29/04* (2013.01); *A61L 29/085* (2013.01); *A61M 1/3655* (2013.01); *A61M 1/3661* (2014.02); *D03D 3/02* (2013.01); *D03D 13/004* (2013.01); *A61L 27/18* (2013.01); *A61L 27/34* (2013.01); *A61L 27/507* (2013.01); *D10B 2401/06* (2013.01); *F16L 58/10* (2013.01)

(58) Field of Classification Search
CPC ..... A61F 2/06; A61M 1/3661; A61M 1/3655; A61L 27/16; A61L 27/34; A61L 27/18; A61L 27/507; A61L 27/50; A61L 29/04; A61L 29/085; D03D 3/02; D03D 13/005; F16L 58/10
See application file for complete search history.

(56) References Cited

U.S. PATENT DOCUMENTS

| | | | |
|---|---|---|---|
| 2004/0122507 | A1 | 6/2004 | Henderson |
| 2013/0090723 | A1 | 4/2013 | Cully et al. |
| 2014/0198295 | A1* | 7/2014 | Fujisawa .......... B29D 11/00038 264/2.6 |

FOREIGN PATENT DOCUMENTS

| | | |
|---|---|---|
| EP | 0 293 090 A2 | 11/1988 |
| JP | 57-176244 U | 11/1982 |
| JP | 2-98352 A | 4/1990 |
| JP | 9-71749 A | 3/1997 |
| JP | 2970320 B2 | 11/1999 |
| JP | 2001-21093 A | 1/2001 |
| JP | 3591868 B2 | 11/2004 |
| JP | 2005-152178 A | 6/2005 |
| JP | 2005-152181 A | 6/2005 |
| JP | 2006-511282 A | 4/2006 |
| JP | 2009-122457 A | 6/2009 |
| JP | 2015-501173 A | 1/2015 |

OTHER PUBLICATIONS

The Extended European Search Report dated Nov. 10, 2020, of counterpart European Application No. 18775224.9.

* cited by examiner

*Primary Examiner* — Camie S Thompson
(74) *Attorney, Agent, or Firm* — DLA Piper LLP (US)

(57) ABSTRACT

A tubular structure has succeeded in achieving excellent puncture resistance as well as maintenance of flexibility in a base by covering the base with a cover having excellent flexibility. The tubular structure includes a tubular base and a cover which covers the base, wherein the cover includes a copolymer containing a silicone monomer and a polymerizable monomer having a fluoroalkyl group(s) as monomer units.

19 Claims, 2 Drawing Sheets

CYLINDRICAL STRUCTURE

TECHNICAL FIELD

This disclosure relates to a tubular structure.

BACKGROUND

Artificial blood vessel is a medical device used as a replacement for diseased blood vessels in the body such as, for example, blood vessels suffering from arterial sclerosis, or used for forming a bypass. Chronic renal failure patients are normally treated by hemodialysis, and dialysis shunt is used for assuring a sufficient quantity of blood flow for carrying out extracorporeal circulation. Dialysis shunt is a name of an artificial blood vessel used as an artery-vein (A-V) shunt mutually bypassing blood flow from an artery to a vein. Dialysis shunt is often used when blood vessels in the body are weak due to high age of the patient or due to the primary disease such as diabetes or the like, or when grafting with autologous blood vessels is difficult.

However, since it is necessary to perform blood vessel puncture with a dialysis needle 3 times a week on average in hemodialysis treatment, a number of holes are opened through the blood vessel wall. Typical examples of artificial blood vessels used for shunt include artificial blood vessels made of expanded polytetrafluoroethylene (hereinafter referred to as ePTFE). However, the blood vessels made of ePTFE have a problem in that a hole, once formed, is not closed if the ePTFE artificial blood vessel is used as it is, which causes a problem in that bleeding occurs from a puncture after the puncture is generated by a dialysis needle or the like.

To solve this problem, it has been reported to give resistance to puncture by covering the outer surface of the conventional artificial blood vessel made of ePTFE with an elastomer polymer represented by, for example, silicone, polyurethane or polystyrene (JP 2970320 B, JP 2005-152178 A, JP 2015-501173 T, JP 2005-152181 A and JP 2006-511282 T).

Blood vessels in the body have an intima on the inner surface thereof, and thrombus formation is inhibited by the existence of vascular endothelial cells. However, since the conventional artificial blood vessels made of ePTFE have a poor compatibility with cells, not only colonization of the vascular endothelial cells is unlikely to occur, but also a long time is needed until colonization of the vascular endothelial cells and formation of intima.

In view of this, an artificial blood vessel using, as a base, a porous structure composed of polyester fibers having elasticity has been reported to enhance the growth of the vascular endothelial cells into the porous portion and to stabilize the cells in the body for a long time (JP 3591868 B). The outer surface of that artificial blood vessel is covered with a silicone or a polystyrene elastomer to give resistance to puncture, whereby the ability to seal puncture wounds is imparted to the artificial blood vessel.

On the other hand, an artificial blood vessel for internal shunt has been reported, which is prepared by winding a nonwoven fabric composed of a polyurethane having an excellent elasticity around a base to form a tubular body, which retains an excellent elasticity while attaining a leakage rate after puncture of 200 mL/min or less (JP 2-98352 A).

However, the artificial blood vessels described in JP 2970320 B, JP 2005-152178 A, JP 2015-501173 T, JP 2005-152181 A and JP 2006-511282 T have poor flexibility due to the high elasticity of the elastomer polymer used as a cover. With an artificial blood vessel having a poor flexibility, problems such as reduced QOL (Quality of Life) in patients occur due to the difficulty in blood vessel puncture with a dialysis needle, which is carried out when the dialysis is performed, or due to the foreign-body sensation resulting from the implantation of a hard artificial blood vessel.

In the artificial blood vessel described in JP 2970320 B, puncture resistance is imparted by a base wrapped in 10 layers of an ePTFE sheet with a thickness of 80 μm, though no satisfactory water leakiness is obtained. In the artificial blood vessels described in JP 2005-152178 A, JP 2005-152181 A and JP 2006-511282 T, an ePTFE base is coated with a styrene elastomer or a low-molecular-weight polymer composed of ethylene and vinyl acetate and the resulting elastomer layer has an effect to achieve some degrees of kink resistance and puncture resistance, though no satisfactory performance is obtained. In the method disclosed in JP 2015-501173 T which comprises the steps of winding an ePTFE sheet around an ePTFE base and reversing the resulting base, puncture resistance resulting from the compression elasticity generated by the reversion process is imparted to the reversed tube, though no sufficient kink resistance is presumably achieved due to the many layers of the tape wound around the base.

In the artificial blood vessel described in JP 3591868 B, the flexibility of the original base is presumably maintained due to the thin thickness of the silicone layer. According to JP 3591868 B, the artificial blood vessel serves to reduce blood leakage when pierced with a 17-gauge puncture member. However, the artificial blood vessel is insufficient in terms of puncture resistance because dialysis needles often used for dialysis treatment in clinical settings are 16-gauge needles, which means that needles of one size larger are required to puncture blood vessels.

In the artificial blood vessel for internal shunt described in JP 2-98352 A, low water leakiness is achieved by a highly elastic polyurethane, though polyurethane is known to lose its strength when staying in the body for a long period of time and the artificial blood vessel may thus be unable to maintain the puncture resistance for a long period of time.

Accordingly, it could be helpful to provide a tubular structure that reduces water leakiness after getting pierced with a puncture member, without impairing the flexibility of the base.

SUMMARY

We thus provide (1) to (12):
(1) A tubular structure comprising a tubular base and a cover which covers the above-described base, wherein the cover includes a copolymer comprising a silicone monomer and a polymerizable monomer having a fluoroalkyl group(s) as monomer units.
(2) The tubular structure of (1), wherein the above-described silicone monomer is represented by Formula (I):

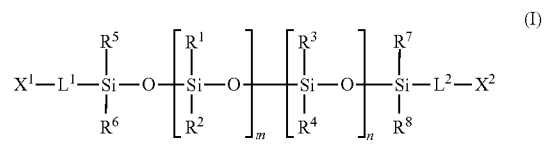

wherein $X^1$ and $X^2$ independently represent a polymerizable functional group; $R^1$ to $R^8$ independently represent hydrogen or a functional group selected from the group consisting of $C_1$-$C_{20}$ alkyl groups, phenyl group, and $C_1$-$C_{20}$ fluoroalkyl groups; $L^1$ and $L^2$ independently represent a divalent group; and m and n independently represent an integer of 0 to 1500 with the proviso that m and n are not simultaneously 0.

(3) The tubular structure of (2), wherein the above-described $X^1$ and $X^2$ are (meth)acryloyl group.

(4) The tubular structure of any of (1) to (3), wherein the polymerizable monomer having a fluoroalkyl group(s) is represented by Formula (II):

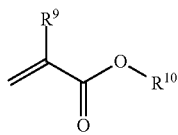

(II)

wherein $R^9$ represents hydrogen or a methyl group; and $R^{10}$ represents a $C_1$-$C_{20}$ fluoroalkyl group.

(5) The tubular structure of any of (1) to (4), which satisfies Expression (1):

$$I^1/I^2 \leq 5.0 \quad (1)$$

wherein $I^1$ represents an absorbance of 1740 to 1780 cm$^{-1}$ due to stretching vibration of C=O originated from ester groups; and $I^2$ represents an absorbance of 1430 to 1470 cm$^{-1}$ due to bending vibration of C—H originated from alkyl groups, when the surface of the above-described cover is subjected to a measurement by single-reflection infrared spectroscopy at a wavelength of 2.5 to 25 μm and an angle of incidence of 45°.

(6) The tubular structure of any of (1) to (5), wherein the above-described copolymer has a carboxyl group(s) and/or a hydroxyl group(s).

(7) The tubular structure of (5) or (6), wherein the above-described copolymer comprises a structure represented by Formula (III):

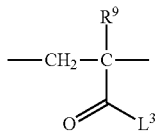

(III)

wherein $R^9$ represents hydrogen or a methyl group, and $L^3$ represents a monovalent group.

(8) The tubular structure of any of (1) to (7), wherein the above-described base is composed of a polyester, polyurethane, or polytetrafluoroethylene.

(9) The tubular structure of any of (1) to (8), wherein the above-described tubular base is a tubular woven fabric comprising warp yarns and weft yarns, wherein the tubular woven fabric has a difference in outer diameter in the direction of the warp yarns of 10% or less, and satisfies Expression (2):

$$(L2-L1)/L1 \geq 0.1 \quad (2)$$

wherein L1 represents the gauge length when the tubular woven fabric is compressed with a stress of 0.01 cN/dtex in the direction of the warp yarns in the woven fabric, the gauge marks being drawn on the outer circumference of the woven fabric at a distance of 5 times the maximum outer diameter of the woven fabric, which outer diameter is measured under the state wherein no stress is applied; and L2 represents the gauge length when the fabric is elongated in the direction of the warp yarns with a stress of 0.01 cN/dtex.

(10) The tubular structure of any of (1) to (9), wherein the above-described tubular base is a tubular woven fabric comprising warp yarns and weft yarns, wherein the above-described tubular woven fabric satisfies Expression (3):

$$0.03 \leq (a-b)/a < 0.2 \quad (3)$$

wherein "a" represents the maximum outer diameter of the woven fabric when the woven fabric is compressed in the direction of the warp yarns with a stress of 0.01 cN/dtex; and "b" represents the minimum outer diameter of the woven fabric when the woven fabric is elongated in the direction of the warp yarns with a stress of 0.01 cN/dtex.

(11) The tubular structure of any of (1) to (10), which is a medical tube implantable in the body.

(12) The tubular structure of any of (1) to (10), which is an artificial blood vessel.

The tubular structure can reduce water leakiness after getting pierced with a puncture member, without impairing the flexibility of the base, and can be particularly suitably used for a medical tube implantable in the body, particularly for an artificial blood vessel and a dialysis shunt.

EXPLANATION OF SYMBOLS

Figure 1:
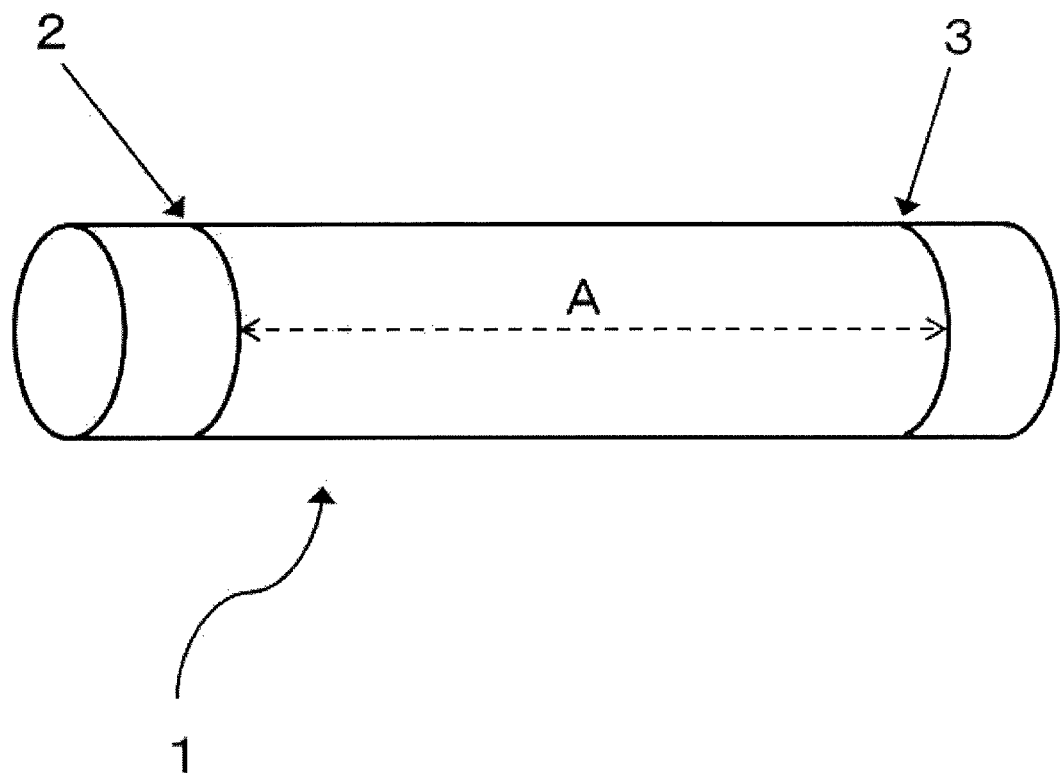
FIG. 1 depicts a diagram for explaining how to draw gauge marks on a tubular woven fabric.

Tubular woven fabric . . . 1; First gauge mark . . . 2; Second gauge mark . . . 3; Load measurement device . . . 4; Platform . . . 5; Compression chuck . . . 6; Compression chuck receiver . . . 7; Elongation chuck . . . 8; Elongation chuck receiver . . . 9; Fixing tape . . . 10; the gauge length drawn at a distance of 5 times the maximum outer diameter of a woven fabric . . . A

DETAILED DESCRIPTION

The tubular structure comprises a tubular base and a cover covering the base, wherein the cover includes a copolymer comprising a silicone monomer and a polymerizable monomer having a fluoroalkyl group(s) as monomer units.

The copolymer refers to a copolymer which can form a cross-linked structure through intermolecular chemical bonding between monomer units having two or more polymerizable functional groups. Examples of the chemical bonding in this respect include, but are not particularly limited to, covalent bonding, ionic bonding, hydrogen bonding, hydrophobic interaction, and π-π stacking; among these types of bonding, covalent bonding is preferred from the viewpoint of insolubilization in various solvents, thermostability, and mechanical properties such as elastic modulus, and elongation.

The above-described copolymer preferably has a water content of not more than 10% by weight, more preferably not more than 5%, still more preferably not more than 2%, still more preferably not more than 1%, because less swelling of the copolymer is desired to occur upon contact with a liquid from the viewpoint of the maintenance of the adhesion with the base. The water content of the copolymer is calculated from the dry weight of a test specimen prepared using the copolymer and the wet weight of the test specimen prepared by immersing the above test specimen in water overnight and then wiping water off the surface, by Expression (A):

Water content=[(weight in wet state)−(weight in dry state)/(weight in wet state)]×100 (A)

The lower limit of the tensile modulus of the above-described copolymer is preferably not less than 0.1 MPa, more preferably not less than 0.2 MPa, still more preferably not less than 0.3 MPa. The higher limit of the tensile modulus of the copolymer is preferably not more than 20, more preferably not more than 10 MPa, still more preferably not more than 0.8 MPa, and most preferably not more than 0.6 MPa.

The lower limit of the tensile elongation (rupture elongation) of the above-described copolymer is not less than 50%, preferably not less than 150%, more preferably not less than 170%, still more preferably not less than 200%, and most preferably not less than 400%. The higher limit of the tensile elongation of the above-described copolymer is not more than 3000%, more preferably not more than 2500%, still more preferably not more than 2000%, most preferably not more than 1000%.

The silicone monomer in the copolymer is preferably a poly(dimethyl siloxane) compound having plural polymerizable functional groups in each monomer. The cover preferably contains as a main component a copolymer which is a copolymer with a compound different from the above-described poly(dimethyl siloxane) compound. The main component refers to a component contained at a concentration of 50% by weight or more relative to the dry weight of the base (100% by weight).

The silicone monomer preferably has a number-average molecular weight of not less than 6,000. We found that a flexible copolymer with excellent mechanical properties such as kink resistance is obtained by limiting the number-average molecular weight of the silicone monomer to a value within this range. The silicone monomer preferably has a number-average molecular weight of 8,000 to 100,000, more preferably 9,000 to 70,000, and most preferably 10,000 to 50,000.

The dispersity of the silicone monomer (the value obtained by dividing the weight-average molecular weight by the number-average molecular weight) is preferably not more than 6, more preferably not more than 3, still more preferably not more than 2, and most preferably not more than 1.5. When the dispersity of the silicone monomer is small, compatibility with other components is promoted and advantages are obtained such as reduction of the amount of extractable components contained in the obtained molded body and reduction in shrinkage rate associated with molding.

The number-average molecular weight of the silicone monomer is a number-average molecular weight determined by gel permeation chromatography (GPC) using chloroform as a solvent and expressed in terms of polystyrene. The weight-average molecular weight and the dispersity (the value obtained by dividing the weight-average molecular weight by the number-average molecular weight) are also determined by the same method.

The silicone monomer is a silicone monomer having a polymerizable functional group(s). For the silicone monomer, the number of polymerizable functional groups per monomer may be one or more, and is preferably two or more from the viewpoint of the ability to easily provide flexibility (a low elastic modulus). In particular, a structure having a polymerizable functional group at each end of a molecular chain is preferred.

Each polymerizable functional group contained in the silicone monomer is preferably a radical polymerizable functional group, more preferably a functional group having a carbon-carbon double bond(s). Preferred polymerizable functional groups include, for example, vinyl group, allyl group, (meth)acryloyl group, α-alkoxymethylacryloyl group, maleic acid residue, fumaric acid residue, itaconic acid residue, crotonic acid residue, isocrotonic acid residue, and citraconic acid residue. Among these, (meth)acryloyl group is most preferred because it is highly polymerizable.

The term "(meth)acryloyl" refers to both "methacryloyl" and "acryloyl," and the same is true for terms such as "(meth)acrylic" and "(meth)acrylate."

The silicone monomer is preferably a monomer represented by Formula (I):

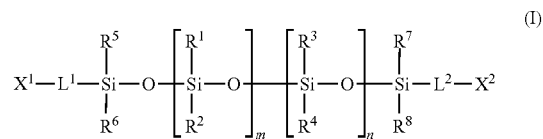

wherein $X^1$ and $X^2$ independently represent a polymerizable functional group; $R^1$ to $R^8$ independently represent hydrogen or one or more functional groups selected from the group consisting of $C_1$-$C_{20}$ alkyl groups, phenyl group, and $C_1$-$C_{20}$ fluoroalkyl groups; $L^1$ and $L^2$ independently represent a divalent group; and m and n independently represent an integer of 0 to 1500 with the proviso that m and n are not simultaneously 0.

Preferably, $X^1$ and $X^2$ each represent, among polymerizable functional groups, a radical polymerizable functional group, which preferably has a carbon-carbon double bond(s). Examples of the polymerizable functional group include vinyl group, allyl group, (meth)acryloyl group, α-alkoxymethylacryloyl group, maleic acid residue, fumaric acid residue, itaconic acid residue, crotonic acid residue, isocrotonic acid residue, and citraconic acid residue. Among these, (meth)acryloyl group is most preferred because it is highly polymerizable.

Preferred specific examples of $R^1$ to $R^8$ are hydrogen; $C_1$-$C_{20}$ alkyl groups such as methyl group, ethyl group, propyl group, isopropyl group, butyl group, t-butyl group, decyl group, dodecyl group, and octadecyl group; phenyl group; and $C_1$-$C_{20}$ fluoroalkyl groups such as trifluoromethyl group, trifluoroethyl group, trifluoropropyl group, tetrafluoropropyl group, hexafluoroisopropyl group, pentafluorobutyl group, heptafluoropentyl group, nonafluorohexyl group, hexafluorobutyl group, heptafluorobutyl group, octafluoropentyl group, nonafluoropentyl group, dodecafluoroheptyl group, tridecafluoroheptyl group, dodecafluorooctyl group, tridecafluorooctyl group, hexadecafluorodecyl group, heptadecafluorodecyl group, tetrafluoropropyl group, pentafluoropropyl group, tetradecafluorooctyl group, pentadecafluorooctyl group, octadecafluorodecyl group, and nonadecafluorodecyl group. Among these, hydrogen and methyl group are further preferred, and methyl group is most preferred, from the viewpoint of the ability to provide suitable mechanical properties.

$L^1$ and $L^2$ are preferably $C_1$-$C_{20}$ divalent groups. Among these divalent groups, L and $L^2$ are preferably any of the groups represented by Formulae (LE1) to (LE12), because use of these groups is advantageous in the production of highly pure products. In each of Formulae (LE1) to (LE12), the points of attachment to a polymerizable functional group $X^1$ or $X^2$ is depicted at the left end, and the points of attachment to a silicon atom is depicted at the right end.

OCH$_2$CH$_2$CH$_2$ (LE1)

NHCH$_2$CH$_2$CH$_2$ (LE2)

OCH$_2$CH$_2$NHCOOCH$_2$CH$_2$CH$_2$ (LE3)

OCH$_2$CH$_2$NHCONHCH$_2$CH$_2$CH$_2$ (LE4)

OCH$_2$CH$_2$CH$_2$CH$_2$ (LE5)

NHCH$_2$CH$_2$CH$_2$CH$_2$ (LE6)

OCH$_2$CH$_2$NHOOOCHCH$_2$CH$_2$CH$_2$CH$_2$ (LE7)

OCH$_2$CH$_2$NHCONHCH$_2$CH$_2$CH$_2$CH$_2$ (LE8)

OCH$_2$CH$_2$OCH$_2$CH$_2$CH$_2$ (LE9)

NHCH$_2$CH$_2$OCH$_2$CH$_2$CH$_2$ (LE10)

OCH$_2$CH$_2$NHCOOCH$_2$CH$_2$OCH$_2$CH$_2$CH$_2$ (LE11)

OCH$_2$CH$_2$NHCONHCH$_2$CH$_2$OCH$_2$CH$_2$CH$_2$ (LE12)

Among these groups represented by Formulae (LE1) to (LE12), the groups represented by Formulae (LE1), (LE3), (LE5), (LE9), and (LE11) are more preferred; the groups represented by Formulae (LE1), (LE3), and (LE5) are further preferred; and the group represented by Formula (LE1) is most preferred.

The letters "m" and "n" independently represent the numbers of each repeating unit. The letters "m" and "n" independently represent an integer of 0 to 1500. The sum (m+n) of values represented by m and n is preferably an integer of not less than 80, more preferably not less than 100, more preferably 100 to 1400, still more preferably 120 to 950, and most preferably 130 to 700.

When $R^1$ to $R^8$ all represent methyl group, n is 0, and m is preferably 80 to 1500, more preferably 100 to 1400, still more preferably 120 to 950, and most preferably 130 to 700. In this example, the value represented by m is determined by the molecular weight of the silicone monomer.

The above-described silicone monomers may be used individually, or two or more of them may be used in combination.

As another compound to be copolymerized with the silicone monomer, a polymerizable monomer having a fluoroalkyl group(s) represented by Formula (II) is preferred:

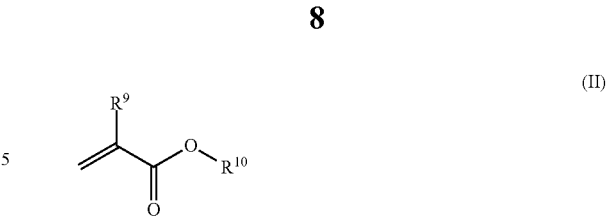

wherein $R^9$ represents hydrogen or a methyl group; and $R^{10}$ represents a $C_1$-$C_{20}$ fluoroalkyl group.

Preferred specific examples of the $C_1$-$C_{20}$ fluoroalkyl group represented by $R^{10}$ are $C_1$-$C_{20}$ fluoroalkyl groups such as trifluoromethyl group, trifluoroethyl group, trifluoropropyl group, tetrafluoropropyl group, hexafluoroisopropyl group, pentafluorobutyl group, heptafluoropentyl group, nonafluorohexyl group, hexafluorobutyl group, heptafluorobutyl group, octafluoropentyl group, nonafluoropentyl group, dodecafluoroheptyl group, tridecafluoroheptyl group, dodecafluorooctyl group, tridecafluorooctyl group, hexadecafluorodecyl group, heptadecafluorodecyl group, tetrafluoropropyl group, pentafluoropropyl group, tetradecafluorooctyl group, pentadecafluorooctyl group, octadecafluorodecyl group, and nonadecafluorodecyl group. $C_2$-$C_8$ fluoroalkyl groups such as trifluoroethyl group, tetrafluoropropyl group, hexafluoroisopropyl group, octafluoropentyl group, and dodecafluorooctyl group, are more preferred; and trifluoroethyl group is most preferred. Hydrophobic interaction due to such fluoroalkyl groups results in attraction of hydrophobic proteins and cells in the body. Thus, when the tubular structure is used for artificial blood vessels and the like, an effect to promote organization of biological systems on the inner surface of the tubular structure can be expected. Additionally, use of such a polymerizable monomer having a fluoroalkyl group(s) causes the resulting copolymer to obtain excellent mechanical properties such as flexibility and kink resistance.

The above-described polymerizable monomers having a fluoroalkyl group(s) may be used individually, or two or more of them may be used in combination.

The content of the polymerizable monomer having a fluoroalkyl group(s) in the copolymer is preferably 10 to 500 parts by weight, more preferably 20 to 400 parts by weight, still more preferably 20 to 200 parts by weight, relative to 100 parts by weight of the silicone monomer. When the amount thereof used is too small, for example, the mechanical properties such as kink resistance, tend to be insufficient.

In addition to the silicone monomer and the polymerizable monomer having a fluoroalkyl group(s), a different monomer may further be used to produce the copolymer in the above-described tubular structure.

The different monomer is preferably a monomer that lowers the glass transition temperature of the copolymer to room temperature or to a temperature equal to or below 0° C. Such a monomer has an effect to reduce the cohesive energy and thus to impart rubber elasticity and flexibility to the copolymer.

The different monomer preferably contains a radical polymerizable functional group, more preferably a polymerizable functional group having a carbon-carbon double bond(s), as the polymerizable functional group. Preferred examples of the polymerizable functional group include vinyl group, allyl group, (meth)acryloyl group, α-alkoxymethylacryloyl group, maleic acid residue, fumaric acid residue, itaconic acid residue, crotonic acid residue, isocrotonic acid residue, and citraconic acid residue; among these, (meth)acryloyl group is most preferred because it is highly polymerizable.

Examples of the different monomer suitable for improving the mechanical properties such as flexibility and kink resistance are alkyl (meth)acrylates; preferably alkyl (meth)acrylates containing a $C_1$-$C_{20}$ alkyl group. Examples thereof include methyl (meth)acrylate, ethyl (meth)acrylate, n-propyl (meth)acrylate, n-butyl (meth)acrylate, tert-butyl (meth)acrylate, isobutyl(meth)acrylate, n-hexyl (meth)acrylate, n-octyl (meth)acrylate, 2-ethylhexyl (meth)acrylate, n-heptyl (meth)acrylate, n-nonyl (meth)acrylate, n-decyl (meth)acrylate, isodecyl (meth)acrylate, n-lauryl (meth)acrylate, tridecyl (meth)acrylate, n-dodecyl (meth)acrylate, cyclopentyl (meth)acrylate, cyclohexyl (meth)acrylate and n-stearyl (meth)acrylate; more preferably n-butyl (meth)acrylate, n-octyl (meth)acrylate, n-lauryl (meth)acrylate, and n-stearyl (meth)acrylate. Among these, alkyl (meth)acrylates containing a $C_1$-$C_{10}$ alkyl group are further preferred.

Furthermore, to improve mechanical properties, dimensional stability, and the like, a below-described monomer(s) may optionally be copolymerized.

Examples of the monomer to improve mechanical properties include aromatic vinyl compounds such as styrene, tert-butylstyrene, and α-methylstyrene, and the like.

Examples of the monomer to improve dimensional stability include ethylene glycol dimethacrylate, diethylene glycol dimethacrylate, triethylene glycol dimethacrylate, polyethylene glycoldimethacrylate, trimethylol propanetrimethacrylate, pentaerythritol tetramethacrylate, bisphenol dimethacrylate, vinyl methacrylate, acrylic methacrylate, and acrylates corresponding to these methacrylates; divinyl benzene, and triallyl isocyanurate.

The different monomers may be used individually, or two or more of them may be used in combination.

The amount of the different monomer to be used is preferably 0.001 to 400 parts by weight, more preferably 0.01 to 300 parts by weight, still more preferably 0.01 to 200 parts by weight, most preferably 0.01 to 30 parts by weight, relative to 100 parts by weight of the silicone monomer. When the amount of the different monomer to be used is too small, it is difficult to achieve the expected effects of the different monomer. When the amount of the different monomer to be used is too large, for example, the mechanical properties such as kink resistance tend to be insufficient.

The above-described cover may further contain components such as a pigment, a coloring agent, a wetting agent, a slipping agent, a pharmaceutical and nutritional supplement components, a compatibilizer component, an antimicrobial component, and a mold releasing agent. Any of the above-described components may be contained in the copolymer in the unreacted or copolymerized form. A coloring agent contained in the cover facilitates the identification of the cover and improves the convenience in handling.

Any of the above-described components contained in the cover in the unreactive or copolymerized form may be contained in the copolymer. When the above-described component is copolymerized, that is, when a component such as a coloring agent having a polymerizable group(s) is copolymerized, since the component is copolymerized with the silicone monomer and with the polymerizable monomer having a fluoroalkyl group(s) and fixed, the possibility of release of the component is reduced, which is preferable.

In the polymerization reaction, a thermal polymerization initiator or a photopolymerization initiator, typically such as a peroxide or an azo compound, is preferably added to facilitate polymerization. When the polymerization is performed by thermal polymerization, a thermal polymerization initiator exhibiting optimal degradation properties at a desired reaction temperature is chosen for use. In general, azo initiators and peroxide initiators having a half-life of 10 hours at a temperature of 40 to 120° C. are suitable. Examples of a photopolymerization initiator used to perform photopolymerization include carbonyl compounds, peroxides, azo compounds, sulfur compounds, halogen compounds, and metal salts. These polymerization initiators are used individually or in combination. The content of the polymerization initiators is preferably up to 5% by weight of the polymerization mixture.

In the polymerization reaction, a polymerization solvent can be used. Various organic and inorganic solvents are applicable as the solvent. Examples of the solvent include water; alcoholic solvents such as methanol, ethanol, n-propanol, isopropanol, n-butanol, isobutanol, t-butanol, t-amyl alcohol, tetrahydrolinalool, ethylene glycol, diethylene glycol, triethylene glycol, tetraethylene glycol, and polyethylene glycol; glycol ether solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether, and polyethylene glycol dimethyl ether; ester solvents such as ethyl acetate, butyl acetate, amyl acetate, ethyl lactate, and methyl benzoate; aliphatic hydrocarbon solvents such as n-hexane, n-heptane, and n-octane; alicyclic hydrocarbon solvents such as cyclohexane and ethylcyclohexane; ketone solvents such as acetone, methyl ethyl ketone, and methyl isobutyl ketone; aromatic hydrocarbon solvents such as benzene, toluene, and xylene; and petroleum solvents. These solvents may be used individually, or two or more of them may be used in combination.

The cover in the above-described tubular structure preferably has a thickness of not more than 1,000 μm, more preferably not more than 800 μm, and most preferably not more than 600 μm.

To reduce water leakiness after getting pierced with a puncture member, the copolymer exposed on the surface of the cover in the above-described tubular structure more preferably has a carboxyl group(s) and/or a hydroxyl group(s). Introduction of a carboxyl group(s) or a hydroxyl group(s) into a copolymer to change the copolymer to one having a carboxyl group(s) or a hydroxyl group(s) is achieved by, but not particularly limited to, hydrolyzing the copolymer existing on the surface of the cover by surface treatment. Examples of the hydrolysis method include acid treatment, alkali treatment, and plasma treatment; among these, alkali treatment is preferred from the viewpoint of reaction cost and laboratory equipment. By treating the surface of an obtained tubular structure with an alkali solution, the alkyl (meth)acrylate ester bonds and siloxane bonds in the copolymer on the surface of the cover are hydrolyzed, and the copolymer is turned into a copolymer containing a carboxyl group(s) or a hydroxyl group(s).

Although not particularly limited, when the copolymer exposed on the surface of the cover in the above-described tubular structure has a carboxyl group(s) or a hydroxyl group(s), the copolymer can be hydrated and swelled in the body to close a hole created when the tubular structure is pierced with a puncture member.

The copolymer may at least partially contain a structure represented by Formula (III). The copolymer preferably has a carboxyl group(s) and/or a hydroxyl group(s):

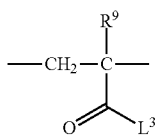

(III)

wherein R⁹ represents hydrogen or a methyl group, and $L^3$ represents a monovalent group.

$L^3$ is preferably a functional group selected from the group consisting of groups represented by Formulae (LE13) to (LE15):

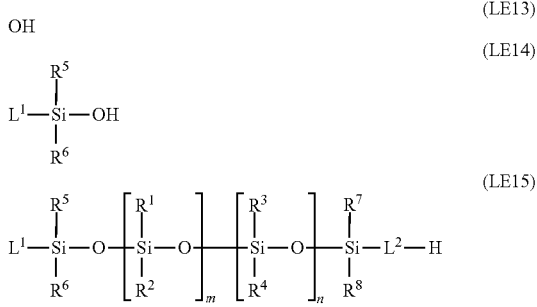

wherein $R^1$ to $R^8$ independently represent hydrogen or one or more functional groups selected from the group consisting of $C_1$-$C_{20}$ alkyl groups, phenyl group, and $C_1$-$C_{20}$ fluoroalkyl groups; $L^1$ and $L^2$ independently represent a divalent group; and m and n independently represent an integer of 0 to 1500 with the proviso that m and n are not simultaneously 0.

The group represented by Formula (LE13) may form a salt with, for example, a metal such as lithium, sodium, potassium or magnesium. Preferred specific examples of $R^1$ to $R^8$ in the groups represented by Formulae (LE14) to (LE15) are hydrogen; $C_1$-$C_{20}$ alkyl groups such as methyl group, ethyl group, propyl group, isopropyl group, butyl group, t-butyl group, decyl group, dodecyl group, and octadecyl group; phenyl group; and $C_1$-$C_{20}$ fluoroalkyl groups such as trifluoromethyl group, trifluoroethyl group, trifluoropropyl group, tetrafluoropropyl group, hexafluoroisopropyl group, pentafluorobutyl group, heptafluoropentyl group, nonafluorohexyl group, hexafluorobutyl group, heptafluorobutyl group, octafluoropentyl group, nonafluoropentyl group, dodecafluoroheptyl group, tridecafluoroheptyl group, dodecafluorooctyl group, tridecafluorooctyl group, hexadecafluorodecyl group, heptadecafluorodecyl group, tetrafluoropropyl group, pentafluoropropyl group, tetradecafluorooctyl group, pentadecafluorooctyl group, octadecafluorodecyl group, and nonadecafluorodecyl group. Among these, hydrogen and methyl group are further preferred, and methyl group is most preferred, from the viewpoint of the ability to provide suitable mechanical properties.

$L^1$ and $L^2$ are preferably a group represented by Formulae (LE1) to (LE12); among these groups, the groups represented by Formulae (LE1), (LE3), (LE5), (LE9), and (LE11) are more preferred; the groups represented by Formulae (LE1), (LE3), and (LE5) are still more preferred; and the group represented by Formula (LE1) is most preferred. For each of the groups represented by Formulae (LE1) to (LE12), the point of attachment to a silicon atom is depicted at the right end.

The letters "m" and "n" independently represent the numbers of each repeating unit. Preferably, the letters "m" and "n" independently range from 0 to 1500. The sum (m+n) of values represented by m and n is preferably an integer of not less than 80, more preferably not less than 100, still more preferably 100 to 1400, still more preferably 120 to 950, still more preferably 130 to 700.

The following alkali treatment is a method comprising immersing the above-described tubular structure in an aqueous alkali solution at a concentration of 0.01 to 10 M to apply surface treatment to the cover. For example, the treatment may be carried out by immersion in a solution of a base such as sodium hydroxide, potassium hydroxide, or ammonia. Solutions used for the above-described acid and alkali treatments may contain a water-soluble organic solvent such as an alcohol.

The ATR technique (single-reflection infrared spectroscopy) can be used for the surface analysis of the cover which has already undergone the above-described alkali treatment. By subjecting the surface of the cover to a measurement by single-reflection infrared spectroscopy (ATR) at a wavelength of 2.5 to 25 m and an angle of incidence of 45°, the absorbance of 1740 to 1780 $cm^{-1}$ due to stretching vibration of C=O originated from carboxylate esters and the absorbance of 1430 to 1470 $cm^{-1}$ due to bending vibration of C—H originated from alkyl groups can be read from the obtained infrared spectrum.

Application of the above-described alkali surface treatment induces hydrolysis of ester groups in the copolymer on the surface of the cover and results in generation of carboxyl groups, which reduces the absorbance of 1740 to 1780 $cm^{-1}$ originated from esters. On the other hand, no reduction occurs in the absorbance of 1430 to 1470 $cm^{-1}$ due to bending vibration of C—H originated from alkyl groups, which are not hydrolyzed even after the above-described alkali surface treatment. Thus, by dividing an absorbance $I^1$ of 1740 to 1780 $cm^{-1}$ by an absorbance $I^2$ of 1430 to 1470 $cm^{-1}$ the ratio of absorbance of ester group to that of alkyl group $I^1/I^2$ of the copolymer on the surface of the cover after the above-described alkali surface treatment can be obtained. $I^1/I^2$ preferably satisfies Expression (1), and $I^1/I^2$ is preferably not more than 5.0, still more preferably not more than 4.0, and most preferably not more than 3.31:

$$I^1/I^2 \leq 5.0 \qquad (1)$$

wherein $I^1$ represents an absorbance of 1740 to 1780 $cm^{-1}$ due to stretching vibration of C=O originated from ester groups; and $I^2$ represents an absorbance of 1430 to 1470 $cm^{-1}$ due to bending vibration of C—H.

The above-described tubular structure is formed by covering a below-described tubular base with the above-described cover. The cover may cover either the outer or inner surface of the tubular base; only the outer surface is preferably covered when the inner surface utilizes the surface profile of the base; and only the inner surface is preferably covered when the outer surface utilizes the surface profile of the base.

As the method of covering the tubular base with the above-described cover, any known method can be used. For example, a method in which a round bar-shaped or plate-shaped polymer is first obtained and then the polymer is processed into a desired shape by cutting work or the like, the mold polymerization method, and the spin-cast polymerization method and the like can be used.

As an example, a method is contemplated, in which a round bar is inserted into a tubular base and the resulting base with the inserted round bar is placed into a tubular mold; then, one port of the mold is sealed with a rubber stopper and a monomer mixture solution is introduced into the gap between the inner wall of the mold and the base from the other port of the mold; subsequently, the introduced monomer materials are polymerized by exposure to active rays such as ultraviolet rays, visible rays, or combinations thereof, or to heat in an oven, a liquid bath or the like. For the polymerization method, a method in which two different polymerization techniques are used in combination is also contemplated. That is, a photopolymerization process may be followed by a thermal polymerization process, or vice versa. In a specific method of photopolymerization, a monomer mixture solution is irradiated by light including ultraviolet rays such as light from a mercury lamp or an ultraviolet lamp (for example, FL15BL; Toshiba Corporation) for a short period of time (normally one hour or shorter). In a specific method of thermal polymerization, conditions that enable the temperature of a monomer mixture solution to rise gradually from room temperature to a temperature of 60° C. to 200° C. for several hours or several tens hours are suitable to increase the reproducibility.

Examples of the material used for the above-described tubular mold include, but are not particularly limited to, glass, polyethylene, polypropylene, polytetrafluoroethylene, polystyrene, and stainless steel. Among these materials, glass, polyethylene, and polypropylene are more preferred, and polypropylene is most preferred, from the viewpoint of transparency suitable for photopolymerization and chemical resistance.

Examples of the material used for the round bar inserted into the above-described tubular base include polyethylene, polypropylene, polytetrafluoroethylene, and stainless steel. Among these materials, polytetrafluoroethylene, polypropylene and stainless steel are more preferred, and stainless steel is most preferred, from the viewpoint of durability and chemical resistance.

A step of removing residual monomers and a used polymerization solvent may be included, which follows the steps of polymerizing the above-described monomer materials, by immersing the resulting polymer in an alcohol, and heating the polymer to a temperature of 50 to 120° C. Preferred specific examples of the alcohol to be used include methanol, ethanol, n-propanol, isopropanol, n-butanol, isobutanol, t-butanol and ethylene glycol. Among these alcohols, methanol, ethanol, n-propanol and isopropanol are more preferred, and isopropanol is most preferred, from the viewpoint of properties that enable easy removal by vacuum drying. These solvents may be used individually, or two or more of them may be used in combination. The heating temperature under immersion in an alcohol is more preferably 60 to 100° C., most preferably 70 to 90° C.

Examples of the material used for the tubular base used for the above-described tubular structure include polyester, polytetrafluoroethylene, and polyurethane. Among these materials, polytetrafluoroethylene and polyester are preferred from the viewpoint of flexibility, kink resistance, and elasticity. Furthermore, polyester is particularly preferably used from the viewpoint of biocompatibility.

The base used for the above-described tubular structure comprises warp yarns and weft yarns interwoven with each other, and does not require crimping, which is usually performed on a vascular prosthesis. Therefore, the variation in the outer diameter along the warp direction of the tubular woven fabric can be made to be within 10%. The "variation in the outer diameter" as described in the expression "variation in the outer diameter is within 10%" is assessed as follows. First, the outer diameter is measured at five locations that are arranged at 50-mm intervals in the warp direction. Then, the minimum value is subtracted from the maximum value, and the difference is divided by the maximum value to determine the variation in the outer diameter, which is expressed in percentage.

When the tubular base used for the above-described tubular structure is a tubular woven fabric comprising warp yarns and weft yarns, the tubular woven fabric preferably satisfies the relation represented by Expression (2):

$$(L2-L1)/L1 \geq 0.1 \qquad (2)$$

wherein

Figure 2:
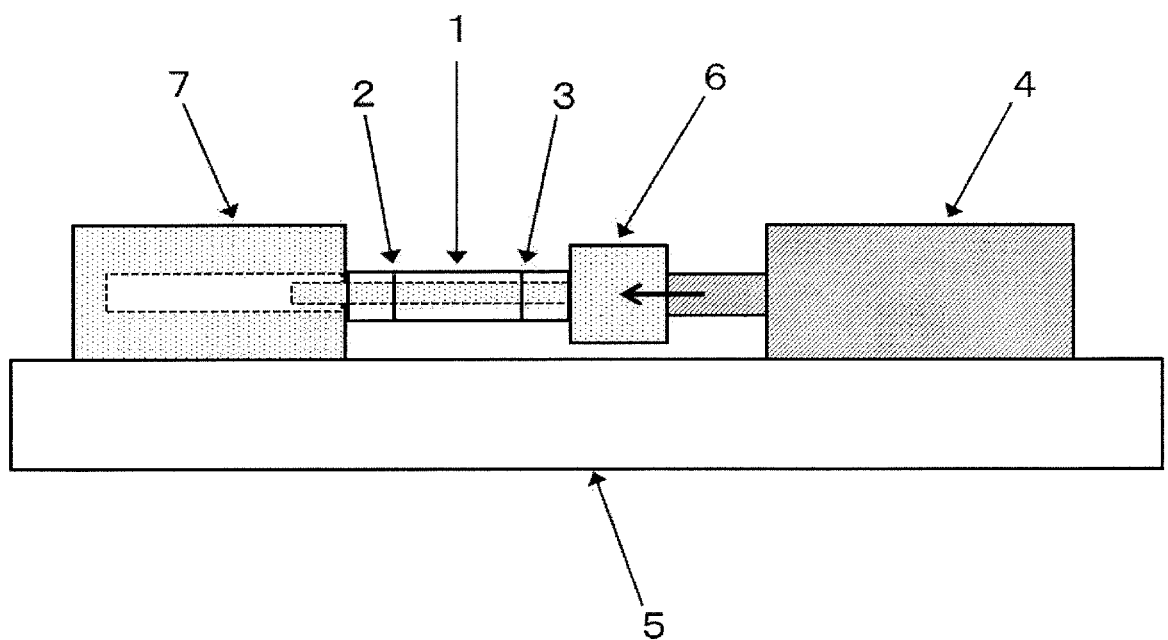
FIG. 2 depicts a schematic diagram of an apparatus for measuring the gauge length on a compressed tubular woven fabric.
Figure 3:
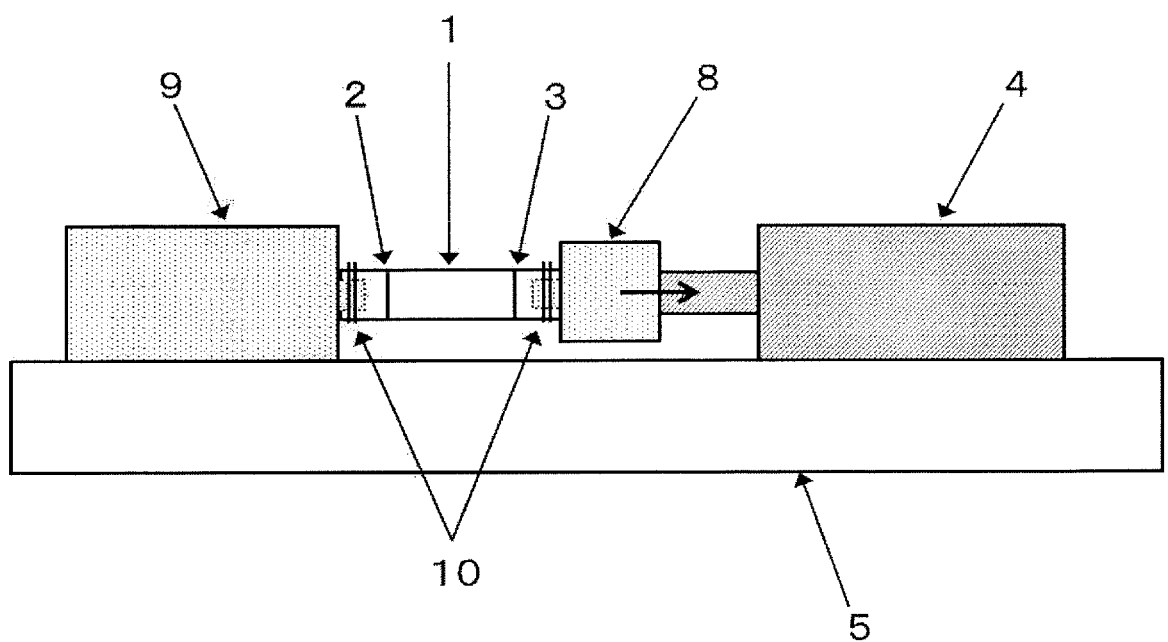
FIG. 3 depicts a schematic diagram of an apparatus for measuring the gauge length on an elongated tubular woven fabric.

L1 is a gauge length (the distance between the first gauge mark 2 and the second gauge mark 3 shown in FIG. 2) of the tubular woven fabric when compressed in the warp direction by applying a stress of 0.01 cN/dtex, as determined after the outer diameter of the tubular woven fabric is measured without applying stress to the tubular woven fabric to determine a maximum outer diameter and then gauge marks are drawn around an outer circumference of the tubular woven fabric so that the gauge marks are separated by a length of five times the maximum outer diameter of the tubular woven fabric; and L2 is the gauge length (the distance between the first gauge mark 2 and the second gauge mark 3 shown in FIG. 3) of the tubular woven fabric when elongated in the warp direction by applying a stress of 0.01 cN/dtex.

For further improved stretch and flexibility, the value calculated by the above-mentioned (L2−L1)/L1 is preferably 0.15 or more, more preferably 0.18 or more. The value is preferably up to 1.0.

When the relation between the gauge lengths L1 and L2 falls within the range defined by Expression (2), the tubular woven fabric exhibits excellent stretch, flexibility and kink resistance (pliability). In more detail, usually, when the tubular woven fabric is pliably bent, the inner side of the bent section of the tubular woven fabric is subjected to a stress in the compression direction, and simultaneously, the outer side of the bent section of the tubular woven fabric is subjected to a stress in the elongation direction. When the relation between the gauge lengths L1 and L2 falls within the above range defined by Expression (2), the outer side is sufficiently elongated with respect to the inner side, exhibiting excellent kink resistance. The stress of 0.01 cN/dtex applied to the tubular woven fabric to elongate or compress the tubular woven fabric typically corresponds to a stress applied by human hands to gently elongate or compress the tubular woven fabric in the warp direction. This indicates that, when the relation between the gauge lengths L1 and L2 falls within the above range, the tubular woven fabric exhibits good handling when bent by human hands, and also shows excellent stretch and flexibility.

Elongation of the tubular woven fabric used for the above tubular structure should be such that, when a user gently stretches the tubular woven fabric by hand, the user can feel a response to elongation. Therefore, the elongation is preferably 30% or less when elongated in the warp direction by applying a stress of 0.01 cN/dtex. The elongation of the tubular woven fabric is more preferably 20% or less, further more preferably about 10%. The lower limit of the elongation is preferably not less than 5%, more preferably not less than 8% so that when a user gently stretches the tubular woven fabric by hand, the user can feel a response to elongation.

It is preferred that Expression (3) be satisfied:

$$0.03 \leq (a-b)/a < 0.2 \qquad (3)$$

wherein a change index (c) defined by

Change index, $c=(a-b)/a$ is preferably 0.03 or more and less than 0.2, more preferably 0.05 or more and less than 0.15, and
wherein
a is the maximum outer diameter of the tubular woven fabric when compressed in the warp direction by applying a stress of 0.01 cN/dtex, and
b is the minimum outer diameter of the tubular woven fabric when elongated in the warp direction by applying a stress of 0.01 cN/dtex.

When the relation between the maximum outer diameter (a) and the minimum outer diameter (b) falls within the range defined by Expression (3), the change in the inner diameter of the tubular woven fabric will be small even when elongation and compression simultaneously occur due to a movement such as bending, and therefore a constant flow passage is ensured. The irregularity of the inner surface of the tubular woven fabric is preferably 100 μm or less, more preferably 80 μm or less, further more preferably 60 μm or less. The lower limit is preferably 3 m or more to facilitate the formation of endothelium when the tubular woven fabric is used as a vascular prosthesis. The tubular woven fabric having an inner surface with an irregularity within the above range will not cause turbulent flow of a fluid passing through the tubular woven fabric even when the inner diameter is small. Especially when used as a vascular prosthesis having a small inner diameter, the tubular woven fabric provides advantages of causing no turbulent flow of blood or being less likely to cause thrombus formation. The tubular woven fabric is preferably not crimped into circumferential corrugations. The tubular woven fabric having no circumferential corrugations has a smooth inner surface and does not cause turbulent flow even when a fluid passes through a narrow passage. Especially when used as a vascular prosthesis having a small inner diameter, the tubular woven fabric provides advantages of causing no turbulent flow of blood or being less likely to cause thrombus formation. The phrase "having no circumferential corrugations" means that a tubular textile does not have circumferential corrugations formed by heat setting with an inserted core rod having spiral or annular corrugations, or that a tubular textile is not finished with pleating.

The warp and weft yarns that are used to produce the tubular woven fabric used for the above tubular structure are preferably made of synthetic fibers such as nylon fibers and polyester fibers. The warp and weft yarns are more preferably the so-called non-elastic yarns. The term "non-elastic yarn" refers to a yarn made of fibers not having the so-called rubber-like elasticity, and is a type of yarn different from the so-called elastic yarns having rubber-like elasticity, which are made of a material excellent in stretch and resilience such as a thermoplastic elastomer, including polyether elastomers, polysulfide elastomers, polyurethane elastomers and the like. The fiber used for the above tubular woven fabric is preferably a non-elastic polyester fiber yarn, which has strength and dimensional stability. Examples of the non-elastic polyester fiber yarn include a yarn made of fibers of polyethylene terephthalate, polybutylene terephthalate, polypropylene terephthalate, a copolymer thereof or the like.

The tubular woven fabric used for the above tubular structure has stretch. Thus, the woven fabric may be produced using elastic yarns or non-elastic yarns. The above tubular woven fabric can be produced, for example, as follows.

In the weaving process, at least two types of warp yarns, i.e., warp yarn A and warp yarn B, are preferably used. These warp yarns are also preferably non-elastic yarns as described above. The warp yarn A may be a yarn made of synthetic fibers such as nylon fibers and polyester fibers. Especially preferred is a non-elastic polyester fiber yarn having strength and dimensional stability. Examples of the non-elastic polyester fiber yarn include a yarn made of fibers of polyethylene terephthalate, polybutylene terephthalate, polypropylene terephthalate, a copolymer thereof or the like. The warp yarn A, which constitutes the woven fabric, may be a directly spun microfiber yarn, or a microfiber yarn formed by removal of the sea component of sea-island composite fibers. The synthetic fiber yarn arranged in the warp direction is preferably a multifilament yarn containing filaments, wherein a part or all of the filaments have a diameter of 5 μm or less. When the diameter of the filaments is in the above range, the resulting tubular woven fabric has improved flexibility and a denser structure.

The warp yarn B is preferably a soluble yarn. The soluble yarn is a yarn made of fibers that are soluble in a solvent such as water and an alkaline solution. Specific examples of the soluble yarn include, but are not limited to, water-soluble fibers such as polyvinyl alcohol fibers; and easily alkali-soluble fibers such as polyester fibers containing a third copolymerized component such as isophthalic acid, sodium 5-sulfoisophthalate and methoxy polyoxyethylene glycol, and polylactic acid fibers. The warp yarn B may be a temporary yarn that is to be removed after weaving process.

The total fineness of each warp yarn is preferably 560 dtex or less, more preferably 235 dtex or less, further more preferably 100 dtex or less. The weave density of the warp yarn A after post-processing is preferably 300 ends/inch (2.54 cm) or less, more preferably 280 ends/inch (2.54 cm) or less, further more preferably 250 ends/inch (2.54 cm) or less.

At least two types of weft yarns, i.e., weft yarn C and weft yarn D, are preferably used. When at least two types of weft yarns are used, the tubular woven fabric is preferably a double layer woven fabric. Preferably, in the double layer woven fabric, the weft yarn C is arranged in the inner layer of the tubular woven fabric, and the weft yarn D is arranged in the outer layer of the tubular woven fabric. The weft yarn C arranged in the inner layer and the weft yarn D arranged in the outer layer may each be a yarn made of synthetic fibers such as nylon fibers and polyester fibers, and is each preferably a non-elastic yarn. Especially preferred is a non-elastic polyester fiber yarn having strength and dimensional stability. Examples of the non-elastic polyester fiber yarn include a yarn made of fibers of polyethylene terephthalate, polybutylene terephthalate, or polypropylene terephthalate.

The weft yarn C is preferably a directly spun microfiber yarn and may be arranged as it is in the inner layer in the weaving process. Alternatively, the weft yarn C may be a sea-island composite fiber yarn and may be arranged in the inner layer in the weaving process, and subsequently the sea component may be removed to give microfibers. Some or all of the weft yarns C preferably have a single filament diameter of not more than 5 μm. When the diameter of the filaments is in the above range, the resulting tubular woven fabric has improved flexibility and a denser structure.

The diameter of filaments contained in the weft yarn D arranged in the outer layer is preferably 10 to 20 μm. When the diameter of the filaments is in the above range, the outer layer is stiffer than the inner layer, is resistant to deterioration by hydrolysis, and has improved durability. The total fineness of each weft yarn is preferably 560 dtex or less, more preferably 235 dtex or less, further more preferably 100 dtex or less. The weave density of each weft yarn after post-processing is preferably 200 picks/inch (2.54 cm) or less, more preferably 180 picks/inch (2.54 cm) or less, further more preferably 150 picks/inch (2.54 cm) or less.

In the weaving process, preferably, the tension of the warp yarn B is high, whereas the tension of the warp yarn A is low to the extent that lowering of the tension does not prevent the shedding of the warp yarns. For example, the tension of the warp yarn B is preferably 0.5 to 1.5 cN/dtex, and the tension of the warp yarn A is preferably 0.05 to 0.15 cN/dtex. The warp yarn A and the warp yarn B are preferably arranged in an alternating pattern of 2 to 10 ends of the warp yarn A and one end of the warp yarn B. Generally, in weaving process for a high-density woven fabric, when the warp tension is lowered to increase the crimp percentage of the warp yarns, the weft density is difficult to increase due to possible occurrence of bumping (slack pick). However, according to the above example, the weft yarns are firmly held by the warp yarn A while the warp yarn B serving as a fulcrum, and in this way, bumping is prevented. Consequently, the crimp percentage of the warp yarn A can be increased, and by removal of the warp yarn B after weaving, flexibility is imparted to the tubular woven fabric. The warp yarn B is preferably arranged between the weft yarn C arranged in the inner layer and the weft yarn D arranged in the outer layer. The at least two types of weft yarns, i.e., the weft yarn C and the weft yarn D arranged in the inner layer and the outer layer of the tubular woven fabric, respectively, have different circumferences, which leads to structural strain. Due to the structural strain, the tubular woven fabric has an elongation capacity.

The inner diameter of the tubular woven fabric is preferably 100 mm or less, more preferably 50 mm or less, further more preferably 10 mm or less. The preferred lower limit is about 1.5 mm for the weaving process to be successful.

The post-processing preferably includes, for example, the following steps. The example below exemplifies when the inner diameter of the tubular woven fabric is 3 mm.

(a) Hot Water Washing

The tubular woven fabric is washed with hot water to remove oil on the yarns and to allow the warp yarn B to shrink. Hot water washing is preferably performed at 80 to 98° C. for 15 to 40 minutes.

(b) Pre-Heat Setting

The dimensions of the warp yarn A having an increased crimp percentage due to shrinkage of the warp yarn B are stabilized by pre-heat setting. A round rod with an outer diameter of 2.8 mm is inserted into the tubular woven fabric, then both ends of the fabric are fastened on the rod with a wire or another material, and the tubular woven fabric is heated. The pre-heat setting is preferably performed at 160 to 190° C. for 3 to 10 minutes. The round rod may be made of, for example, stainless steel.

(c) Removal of Sea Component

As needed, the sea component of the warp yarn A and the weft yarn C is removed, and the warp yarn B is dissolved and removed.

The removal of the sea component and the dissolving and removal of the warp yarn B are performed by the following steps.

(c-1) Acid Treatment

The sea component of the sea-island composite fibers is made brittle by acid treatment. The acid may be, for example, maleic acid. The treatment is preferably performed at a concentration of 0.1 to 1% by mass at 100 to 150° C. for 10 to 50 minutes. When sea-island composite fibers are not used, acid treatment can be omitted.

(c-2) Alkali Treatment

The sea component of the sea-island composite fibers that has been made brittle by the acid treatment as well as the soluble yarn are dissolved by alkali treatment. The alkali may be, for example, sodium hydroxide. The treatment is preferably performed at a concentration of 0.5 to 2% by mass at 70 to 98° C. for 60 to 100 minutes.

(d) Heat Setting (First Stage)

The first heat setting is performed to fully restore the crimp of the warp yarn that has been relaxed by the sea component removal. A round rod with an outer diameter of 3 mm is inserted into the tubular woven fabric. The tubular woven fabric is compressed as much as possible in the warp direction to the extent that wrinkles do not appear, and both ends of the fabric are fastened on the rod with a wire or another material. The fabric is then heated. The first heat setting is preferably performed at 160 to 190° C. for 3 to 10 minutes. The round rod may be made of, for example, stainless steel.

(e) Heat Setting (Second Stage)

The second heat setting is performed on the tubular woven fabric to provide a shrinkage allowance and to stabilize the bending points of the crimp. The second heat setting may be omitted. A round rod with an outer diameter of 3 mm is inserted into the tubular woven fabric. The tubular woven fabric is elongated by 20 to 50% in the warp direction, and both ends of the fabric are fastened on the rod with a wire or another material. The fabric is then heated. The second heat setting is preferably performed at a temperature 10 to 20° C. lower than the first heat setting temperature for 3 to 10 minutes. The round rod may be made of, for example, stainless steel.

The thus produced tubular woven fabric has a less irregular inner surface and exhibits excellent stretch, flexibility and kink resistance (pliability).

When the above tubular structure is used as a vascular prosthesis, the tubular base preferably has an antithrombogenic property on the inner surface that is to be in contact with blood. The antithrombogenic material layer is preferably formed by binding a compound having anticoagulant activity to the inner surface. The term "antithrombogenic" refers to a property that prevents blood coagulation on a surface in contact with blood, for example, the ability to inhibit platelet aggregation or blood coagulation, which proceeds through activation of blood coagulation factors such as thrombin. The antithrombogenic surface may be formed by any method, including but not limited to, a method involving covalent binding of heparin or a heparin derivative to a modified inner surface of the tubular base (JP 2009-545333 A, JP Patent No. 4152075 and JP Patent No. 3497612); a method involving ionic binding of heparin or a heparin derivative to the inner surface of the tubular base, and a method involving applying heparin or a heparin derivative contained in a gel such as collagen and gelatin to the inner surface of the tubular base (JP Patent No. 3799626 and JP H08-24686 B); a method involving coating of the inner surface of the tubular base with a segmented polyurethane by impregnating the tubular base with the segmented polyurethane dissolved in an organic solvent (JP H07-265338 A); a method involving attachment of a compound that inhibits blood coagulation factors involved in blood coagulation reaction or a compound that inhibits thrombin or other factors involved in thrombus formation to the inner surface of the tubular base (JP Patent No. 4461217, WO 08/032758 and WO 12/176861); and other methods. Of these methods, preferred is a method involving ionic binding of heparin or a heparin derivative to the inner surface of the tubular base.

The antithrombogenic material is preferably a compound having anticoagulant activity. The compound having anticoagulant activity may be any compound that has inhibitory effect on platelet aggregation or blood coagulation, which proceeds through the activation of blood coagulation factors such as thrombin. Examples of the compound include aspirin, clopidogrel sulfate, prasugrel sulfate, ticlopidine hydrochloride, dipyridamole, cilostazol, beraprost sodium, limaprost alfadex, sodium ozagrel, sarpogrelate hydrochloride, ethyl icosapentate, trapidil, warfarin potassium, heparin sodium, heparin potassium, dalteparin sodium, parnaparin sodium, reviparin sodium, rivaroxaban, apixaban, edoxaban, dabigatran, argatroban, dextran sulfate, polyvinyl sulfonate, polystyrene sulfonate and the like. Of these compounds, preferred is a sulfur-containing anionic compound having anticoagulant activity.

When an anionic compound with anticoagulation activity is used as the compound with anticoagulation activity, the antithrombogenic material preferably further contains a cationic polymer in addition to the compound with anticoagulation activity. In particular, the antithrombogenic material more preferably contains a cationic polymer containing, as a monomer unit, a compound selected from the group consisting of alkyleneimines, vinyl amines, allylamine, lysine, protamines, and diallyl dimethyl ammonium chloride.

These monomer units have a cationic nitrogen atom, and their polymers are cationic. On the other hand, the sulfur-containing compound having anticoagulant activity is anionic, and can therefore bind to the cationic polymer by ionic bonding. Examples of the sulfur-containing anionic compound having anticoagulant activity include heparin and heparin derivatives, dextran sulfate, polyvinyl sulfonate, and polystyrene sulfonate. Preferred are heparin and heparin derivatives. The heparin and heparin derivatives may be purified or unpurified, and are not particularly limited as long as they inhibit blood coagulation reaction. Examples of the heparin and heparin derivatives include heparin that is commonly used for clinical applications, unfractionated heparin, low-molecular-weight heparin, and heparin with high affinity to antithrombin III. Specific examples of heparin include "heparin sodium" (Organon API, Inc.) and the like.

The cationic polymer may exhibit hemolytic toxicity and the like due to its cationic properties. Therefore, elution of the cationic polymer into the blood is not desirable. Accordingly, the cationic polymer is preferably bound to, more preferably covalently bound to, the inner surface of the tubular base.

The term "covalent bond" means a chemical bond formed by sharing of electrons between atoms. In the above tubular structure, the covalent bond herein refers to a covalent bond between a carbon, nitrogen, oxygen or sulfur atom of the polymer that constitutes the antithrombogenic material and a carbon, nitrogen, oxygen or sulfur atom on the surface of the base. The covalent bond may be a single bond or a multiple bond. Examples of the covalent bond include, but are not limited to, an amine bond, an azide bond, an amide bond, an imine bond and the like. Of these, an amide bond is preferred because the covalent bond is easy to form and the bond has high stability and other advantages.

The cationic polymer may be a homopolymer or a copolymer. When the cationic polymer is a copolymer, the copolymer may be a random copolymer, a block copolymer, a graft copolymer, or an alternating copolymer. Of these, a block copolymer containing successively repeating units containing a nitrogen atom is preferred because strong ionic bonds are formed by interaction between the blocks and the sulfur-containing anionic compound having anticoagulant activity.

The term "homopolymer" means a macromolecular compound obtained by polymerization of a single type of monomer unit. The term "copolymer" means a macromolecular compound obtained by copolymerization of two or more types of monomers. The term "block copolymer" means a copolymer having a molecular structure in which at least two types of polymers having different repeating units are covalently bound to each other to form a longer chain. The term "block" means each of the at least two types of polymers that have different repeating units and constitute the block copolymer.

In the above tubular structure, the cationic polymer herein may be linear or branched. In the above tubular structure, a branched cationic polymer is preferred because it can form a large number of more stable ionic bonds together with the sulfur-containing anionic compound having anticoagulant activity.

In the above tubular structure, the cationic polymer herein has at least one functional group selected from primary, secondary and tertiary amino groups and a quaternary ammonium group. Of these, the cationic polymer having a quaternary ammonium group is preferred because a quaternary ammonium group forms stronger ionic interaction with the sulfur-containing anionic compound having anticoagulant activity than a primary, secondary or tertiary amine group, and therefore allows easier control of the elution rate of the sulfur-containing anionic compound having anticoagulant activity.

In the above tubular structure, the number of carbon atoms in the three alkyl groups of the quaternary ammonium group is not particularly limited. However, the number of carbon atoms contained in the three alkyl groups should be selected to ensure that the quaternary ammonium group does not have high hydrophobicity or large steric hindrance so that the quaternary ammonium group effectively forms ionic bonds with the sulfur-containing anionic compound having anticoagulant activity. The number of carbon atoms contained in the three alkyl groups should also be selected to ensure that hemolytic toxicity is minimized. Accordingly, the number of carbon atoms contained in a single alkyl group bound to the nitrogen atom of the quaternary ammonium group is preferably 1 to 12, more preferably 2 to 6. The number of carbon atoms contained in each of the three alkyl groups bound to the nitrogen atom of the quaternary ammonium group may be the same as or different from each other.

In the above tubular structure, the cationic polymer herein is preferably a polyalkyleneimine. Use of a polyalkyleneimine as the cationic polymer is advantageous in that it adsorbs a large amount of the sulfur-containing anionic compound having anticoagulant activity by ionic interaction. Examples of the polyalkyleneimine include polyethyleneimine (hereinafter called "PEI"), polypropyleneimine, polybutyleneimine, and alkoxylated polyalkyleneimine. Of these, PEI is best preferred.

Specific examples of PEI include "LUPASOL" (registered trademark) (BASF SE), and "EPOMIN" (registered trademark) (Nippon Shokubai Co., Ltd.). The PEI may be a copolymer with another monomer or a modified PEI polymer as long as the effects of the above tubular structure are not impaired. The term "modified polymer" means a polymer that has the same constituent monomers as in the original cationic polymer but some of the constituent monomers have undergone, for example, radical decomposition or recombination by irradiation as described later.

In the above tubular structure, if the weight average molecular weight of the cationic polymer is excessively small, the molecular weight of the cationic polymer is smaller than that of the sulfur-containing anionic compound having anticoagulant activity. Consequently, stable ionic bonds cannot be formed and the desired antithrombogenicity is less likely to be achieved. On the other hand, if the weight average molecular weight of the cationic polymer is excessively large, the sulfur-containing anionic compound having anticoagulant activity is encapsulated in the cationic polymer, and the antithrombogenic material is buried under the cationic polymer. Accordingly, the weight average molecular weight of the cationic polymer is preferably 600 to 2,000,000, more preferably 1,000 to 1,500,000, further more preferably 10,000 to 1,000,000. The weight average molecular weight of the cationic polymer can be measured by, for example, gel permeation chromatography or the light scattering method.

The production process of the antithrombogenic material will be described below. The tubular base may be coated with the antithrombogenic material by, for example, immersing the base in a solution containing the sulfur-containing anionic compound having anticoagulant activity and a polymer containing, as a monomer unit, a compound selected from the group consisting of alkylene imines, vinyl amines, allylamine, lysine, protamines, and diallyl dimethyl ammonium chloride. Alternatively, the sulfur-containing anionic compound having anticoagulant activity may be partially or fully reacted with the polymer to give an antithrombogenic material, and then the inner surface of the base may be coated with the antithrombogenic material to form an antithrombogenic material layer on the inner surface of the base.

To achieve efficient antithrombogenicity on the surface of the base, preferred is a method including the first antithrombogenic material-coating step of covalently binding the cationic polymer containing, as a monomer unit, a compound selected from the group consisting of alkyleneimines, vinyl amines, allylamine, lysine, protamines, and diallyl dimethyl ammonium chloride to the inner surface of the base, and the second antithrombogenic material-coating step of ionically binding the sulfur-containing anionic compound having anticoagulant activity to the cationic polymer.

When the cationic polymer contains primary, secondary and/or tertiary amino groups, the step of quaternizing the cationic polymer to form a quaternary ammonium polymer may be performed after the first antithrombogenic material-coating step to form strong ionic interaction between the polymer and the sulfur-containing anionic compound having anticoagulant activity and easily control the elution rate of heparin.

The production process of the antithrombogenic material by using the above method will be described in more detail below, which method includes the first antithrombogenic material-coating step of covalently binding the cationic polymer containing, as a monomer unit, a compound selected from the group consisting of alkyleneimines, vinyl amines, allylamine, lysine, protamines, and diallyl dimethyl ammonium chloride to the inner surface of the base, and the second antithrombogenic material-coating step of ionically binding the sulfur-containing anionic compound having anticoagulant activity to the cationic polymer.

The covalent binding of the cationic polymer to the inner surface of the base may be performed by any method. When the base has a functional group (e.g., hydroxy, thiol, amino, carboxyl, aldehyde, isocyanate, and/or thioisocyanate group and the like), the cationic polymer may be chemically reacted with the functional group to form covalent bonds. For example, when the inner surface of the base has a carboxyl group and the like, the polymer having a hydroxy group, a thiol group, an amino group and the like may be covalently bound to the inner surface of the base; or alternatively, a compound having a hydroxy group, a thiol group, an amino group and the like is first covalently bound to the polymer, and then the polymer may be covalently bound to the inner surface of the base having a carboxyl group and the like.

When the base has no functional group, the inner surface of the base may be treated by plasma, corona discharge and the like, and then the cationic polymer may be covalently bound to the base; or alternatively, the inner surface of the base and the cationic polymer may be irradiated to generate radicals, followed by the recombination reaction to form covalent bonds between the inner surface and the cationic polymer. The radiation may typically be γ-rays or an electron beam. When γ-rays are used, the activity of the γ-radiation source is preferably 2,500,000 to 10,000,000 Ci, more preferably 3,000,000 to 7,500,000 Ci. When an electron beam is used, the accelerating voltage of the electron beam is preferably 5 MeV or more, more preferably 10 MeV or more. The radiation dose is preferably 1 to 50 kGy, more preferably 5 to 35 kGy. The irradiation temperature is preferably 10 to 60° C., more preferably 20 to 50° C.

When the covalent bonds are formed by irradiation, an antioxidant may be used to control the amount of the radicals generated. The term "antioxidant" refers to a molecule that readily donates an electron to another molecule. The antioxidant that is employed is not limited to a particular type, and examples thereof include water-soluble vitamins such as vitamin C; polyphenols; alcohols such as methanol, ethanol, propanol, ethylene glycol, propylene glycol and glycerol; sugars such as glucose, galactose, mannose and trehalose; inorganic salts such as sodium hydrosulfite, sodium pyrosulfite and sodium dithionite; uric acid; cysteine; glutathione; and buffering agents such as bis(2-hydroxyethyl)iminotris(hydroxymethyl)methane (hereinafter called "Bis-Tris"). Preferred are methanol, ethanol, propylene glycol and Bis-Tris, and more preferred are propylene glycol and Bis-Tris, all of which are easy to handle, do not remain as a residue and have other advantages. The antioxidants may be used alone or in combination of two or more types. The antioxidants are preferably added to an aqueous solution.

When polyester fibers are used in the tubular base as constituents, the cationic polymer may be contacted with the tubular woven fabric under heating to introduce covalent bonds between the polymer and the polyester fibers by aminolysis reaction. Introduction of covalent bonds can be done by a different method. Alternatively, ester bonds on the inner surface of the base may be hydrolyzed by acid or alkali treatment to form carboxyl groups, and the carboxyl groups on the inner surface may be allowed to undergo condensation reaction with amino groups present on the cationic polymer to form covalent bonds. In the above methods, the cationic polymer may be directly contacted with the inner surface of the base and allowed to react; or the cationic polymer may first be dissolved in a solvent, then contacted with the inner surface of the base and allowed to react. The solvent is preferably water, an alcohol and the like, and especially preferred is water, which is easy to handle, does not remain as a residue and has other advantages. Yet alternatively, the constituent monomers of the cationic polymer may be contacted with the inner surface of the base and then polymerized, and allowed to react with the inner surface to form covalent bonds.

Heating may be performed by any method, including but not limited to, electric heating, microwave heating, far-infrared heating and the like. When covalent bonds are introduced between the polyester fibers and the cationic polymer by aminolysis reaction, the heating temperature is preferably from a temperature near the glass transition point to the melting point.

A step of hydrolyzing and oxidizing ester bonds on the inner surface of the base having ester groups may be performed before the first antithrombogenic material-coating step. Specifically, the hydrolyzing and oxidizing step is suitably performed by treating the inner surface with an acid or alkali and an oxidant. To increase the amount of the cationic polymer coating to enhance antithrombogenicity without inducing activation of complements, the hydrolyzing and oxidizing step is preferably performed by treating the inner surface with an acid or alkali and an oxidant.

When the hydrolyzing and oxidizing step of ester bonds on the inner surface of the base having ester groups is performed using an acid or alkali and an oxidant, either a treatment method with a combination of an acid and an oxidizing agent or a treatment method with a combination of an alkali and an oxidizing agent may be used, and a combination of an acid and an oxidant is preferred. Alternatively, the inner surface of the base may be treatment with an alkali, followed by treatment with an acid and an oxidant.

The acid that is employed is not limited to a particular type, and examples thereof include inorganic acids such as hydrochloric acid, hydrobromic acid, hydroiodic acid, hypochlorous acid, chlorous acid, perchloric acid, sulfuric acid, fluorosulfonic acid, nitric acid, phosphoric acid, hexafluoroantimonic acid, tetrafluoroboric acid, chromic acid and boric acid; sulfonic acids such as methanesulfonic acid, ethanesulfonic acid, benzenesulfonic acid, p-toluenesulfonic acid, trifluoromethanesulfonic acid and sodium polystyrene sulfonate; carboxylic acids such as acetic acid, citric acid, formic acid, gluconic acid, lactic acid, oxalic acid and tartaric acid; vinyl carboxylic acids such as ascorbic acid and Meldrum's acid; nucleic acids such as deoxyribonucleic acids and ribonucleic acids; and the like. Preferred are hydrochloric acid and sulfuric acid, which are easy to handle.

The base that is employed is not limited to a particular type, and examples thereof include hydroxides of alkali metals such as lithium hydroxide, sodium hydroxide, potassium hydroxide, rubidium hydroxide and cesium hydroxide; hydroxides of tetraalkylammoniums such as tetramethylammonium hydroxide and tetraethylammonium hydroxide; hydroxides of alkaline earth metals such as calcium hydroxide, strontium hydroxide, barium hydroxide, europium hydroxide and thallium hydroxide; hydroxides of ammine complexes such as guanidine compounds, diamminesilver(I) hydroxide and tetraamminecopper(II) hydroxide; trimethylsulfonium hydroxide; diphenyliodonium hydroxide; and the like. Preferred are lithium hydroxide, sodium hydroxide and potassium hydroxide, which are easy to handle.

The oxidant that is employed is not limited to a particular type, and examples thereof include potassium nitrate; hypochlorous acid; chlorous acid; perchloric acid; halogens such as fluorine, chlorine, bromine and iodine; permanganates such as potassium permanganate, sodium permanganate trihydrate, ammonium permanganate, silver permanganate, zinc permanganate hexahydrate, magnesium permanganate, calcium permanganate and barium permanganate; ceric ammonium nitrate; chromic acid; dichromic acid; peroxides such as hydrogen peroxide solution; Tollens' reagent; sulfur dioxide; and the like. Preferred are permanganates, which have adequate oxidant strength and moderately prevent deterioration of the antithrombogenic material.

Covalent binding of the cationic polymer to the inner surface of the tubular base containing polyester fibers can also be achieved by, for example, condensation reaction using a dehydration condensation agent or the like. The dehydration condensation agent is not limited to a particular type, and examples thereof include carbodiimide compounds such as N,N'-dicyclohexylcarbodiimide, N,N'-diisopropylcarbodiimide, 1-ether-3-(3-dimethylaminopropyl) carbodiimide, 1-ether-3-(3-dimethylaminopropyl) carbodiimide hydrochloride, 1,3-bis(2,2-dimethyl-1,3-dioxolan-4-ylmethyl)carbodiimide, N-{3-(dimethylamino) propyl}-N'-ethylcarbodiimide, N-{3-(dimethylamino) propyl}-N'-ethylcarbodiimide methiodide, N-tert-butyl-N'-ethylcarbodiimide, N-cyclohexyl-N'-(2-morpholinoethyl) carbodiimide metho-p-toluenesulfonate, N,N'-di-tert-butylcarbodiimide, and N,N'-di-p-tricarbodiimide; and triazine compounds such as 4-(4,6-dimethoxy-1,3,5-triazin-2-yl)-4-methylmorpholinium chloride n-hydrate (hereinafter called "DMT-MM").

The dehydration condensation agent may be used together with a dehydration condensation promoting agent. The dehydration condensation promoting agent that is employed is not limited to a particular type, and examples thereof include pyridine, 4-dimethylaminopyridine, triethylamine, isopropylamine, 1-hydroxybenzotriazole and N-hydroxysuccinimide.

The cationic polymer, the dehydration condensation agent, and the dehydration condensation promoting agent may be mixed together to form an aqueous solution to initiate the condensation reaction, or may be separately added in an appropriate order to initiate the condensation reaction. When the cationic polymer contains primary, secondary and/or tertiary amino groups as functional groups, the step of quaternizing the polymer to form a quaternary ammonium polymer may be performed to form strong ionic interaction between the polymer and heparin or a heparin derivative and to easily control the elution rate of heparin.

Quaternization of the cationic polymer to form a quaternary ammonium polymer may be performed before the cationic polymer is covalently bound to the inner surface of the base; or alternatively, quaternization of the cationic polymer to form a quaternary ammonium polymer may be performed after the cationic polymer is covalently bound to the inner surface of the base. However, to form strong ionic interaction between the cationic polymer and the sulfur-containing anionic compound having anticoagulant activity, the quaternary ammonium groups of the cationic polymer are preferably present on the innermost surface of the antithrombogenic material, and therefore quaternization of the cationic polymer to form a quaternary ammonium polymer is preferably performed after the cationic polymer is covalently bound to the inner surface of the base. Specifically, after covalent bonding to the inner surface of the base, the cationic polymer may be directly contacted with an alkyl halide compound such as chloro ether and bromo ether, or a quaternary ammonium salt containing a glycidyl group, or may be contacted with an aqueous solution or an organic solvent containing such an alkyl halide compound or the quaternary ammonium salt.

The second antithrombogenic material-coating step, in which the sulfur-containing anionic compound having anticoagulant activity is ionically bound to the cationic polymer, is preferably performed by contacting the cationic polymer with an aqueous solution of the sulfur-containing anionic compound, but the ionic bonding may be formed by a different method.

As a measure of the antithrombogenicity, the anti-factor Xa activity of the antithrombogenic material may be employed. The term "anti-factor Xa activity" refers to an index of the degree of inhibition of the activity of factor Xa, which promotes the conversion from prothrombin to thrombin. By measuring the anti-factor Xa activity, the amount of heparin or a heparin derivative on the surface of the antithrombogenic material can be determined in terms of the activity unit of heparin or a heparin derivative. For the measurement, "TEST TEAM (registered trademark) Heparin S" (made by Sekisui Medical Co., Ltd.) was used.

If the anti-factor Xa activity is too low, this indicates that the amount of heparin or a heparin derivative on the surface of the antithrombogenic material is too small, and the desired antithrombogenicity cannot be achieved. On the other hand, if the anti-factor Xa activity is too high, the amount of heparin or a heparin derivative on the surface is sufficient to exhibit the desired antithrombogenicity, but the thickness of the antithrombogenic material may be too large and consequently the fine structure of the surface of the base may be impaired. In other words, the total amount of heparin or a heparin derivative coated on the surface of the antithrombogenic material as assessed by the anti-factor Xa activity is preferably 10 mIU/mg to 20000 mIU/mg, more preferably 50 mIU/mg to 10000 mIU/mg, per unit weight of the base. The total amount of heparin coating herein is determined by cutting the base into a size of about 0.5 cm×1 cm, immersing the specimen in 5 mL of human normal plasma, agitating the specimen at 37° C. for 24 hours, measuring the amount of heparin eluted in the human normal plasma and the amount of heparin remaining on the surface of the base, and summing up the amounts.

The cover can cover the above-described tubular structure without compromising the antithrombogenicity of the inner surface by covering only the outer surface of the above-described tubular structure.

Kink resistance of the above-described tubular structure is an index of flexibility. A kink refers to an obviously extremely folded or collapsed portion of an object such as a string, a rod, or a tubular object, which is generated and is hardly reversed, when the object is bent slowly and gradually. Particularly, when the tubular structure is used as an artificial blood vessel, since kink formation in the tubular structure may directly cause occlusion of the blood vessel, sufficient flexibility which hardly allows kink formation in the tubular structure is demanded. As a method of measuring kink resistance, a method of measuring the minimum kink radius according to the guidance of ISO 7198 is available. In the above-described tubular structure, the minimum kink radius measured by the method is preferably not more than 15 mm, more preferably not more than 12 mm, still more preferably not more than 8 mm, and most preferably not more than 5 mm.

The water leakiness of the above-described tubular structure is an index of puncture resistance. The water leakiness refers to the amount of leaked water per unit time determined by measuring the weight of water leaked from a tubular structure with a lumen filled with water and pierced with a puncture member. The water leakiness per puncture event determined by the method is preferably not more than 50 g/min, more preferably not more than 40 g/min, still more preferably not more than 20 g/min, and most preferably not more than 10 g/min.

EXAMPLES

Our structures will now be described in detail by way of Reference Examples, Examples, and Comparative Examples, but this disclosure is not limited thereto. The methods of measuring various properties are as follows.

(1) Fineness and Number of Filaments

The fineness was determined in accordance with 8.3.1 Fineness based on corrected mass (Method A) as specified in JIS L 1013:2010. The number of filaments was determined in accordance with JIS L 1013:2010 8.4.

(2) Diameter of Filaments

The lateral surface of a multifilament yarn used in Examples and Comparative Examples was photographed at 400-fold magnification with a microscope VHX-2000 (KEYENCE CORPORATION) to determine the diameter of the filaments, which was expressed in μm. In a modified cross-section yarn such as a flat yarn, the lateral surface with a minimum width was measured.

(3) Inner Diameter of Tubular Woven Fabric

The inner diameter of a tubular woven fabric was determined in accordance with the guidance of ISO 7198. Briefly, a circular cone with a taper ratio of 1:10 or a smaller taper ratio was placed upright. A tubular woven fabric with one end cut in the radial direction was held above the cone with the end facing down, and allowed to vertically fall on the cone so that the apex of the cone was slipped into the tubular woven fabric. The diameter of the cone at the height where the lower end of the specimen was situated was measured. The inner diameter was measured at five locations at 50-mm intervals in the warp direction by cutting the tubular woven fabric. The maximum and minimum values were used for analysis.

(4) Outer Diameter of Tubular Woven Fabric

The outer diameter of a tubular woven fabric was measured with a caliper. The outer diameter was measured at five locations at 50-mm intervals in the warp direction without applying stress to the tubular woven fabric. The maximum and minimum values were used for analysis. The variation in the outer diameter was determined by subtracting the minimum value from the maximum value, and dividing the difference by the maximum value.

(5) Gauge Length (L1) of Tubular Woven Fabric Under Compression and Gauge Length (L2) of Tubular Woven Fabric Under Elongation The maximum value of the outer diameter of a tubular woven fabric (the maximum outer diameter of the tubular woven fabric when measured without applying stress to the tubular woven fabric) was first determined by the method described in the above (4).

FIG. 1 is an explanatory diagram for drawing gauge marks on a tubular woven fabric. As shown in FIG. 1, a first gauge mark (2) is drawn around the outer circumference of the tubular woven fabric (1) at 5 mm away from one end of the tubular woven fabric. A second gauge mark (3) is then drawn around the outer circumference of the woven fabric at a distance A, which is away from the first gauge mark by a length of five times the maximum outer diameter of the tubular woven fabric. The tubular woven fabric (1) is cut in the radial direction at 5 mm outwardly away from the second gauge mark.

FIG. 2 is a schematic diagram of a device for measurement of the gauge length of the tubular woven fabric under compression. In the device as shown in FIG. 2, HANDY DIGITAL FORCE GAUGE HF-1 (rated capacity: 10 N) made by Japan Instrumentation System Co., Ltd. is placed as a load gauge (force gauge) (4) on a platform (5). The load gauge (4) is equipped with a chuck for compression (6) having a core rod. A receiving portion for compression (7) having a hole capable of receiving the core rod is placed on the platform (5). The tubular woven fabric (1) was placed on the above device by inserting the core rod of the chuck for compression (6) into the tubular woven fabric (1). The tubular woven fabric (1) was then compressed in the warp direction by applying a stress of 0.01 cN/dtex, and the gauge length (L1) (gauge length under compression) was measured with a caliper.

The outer diameter of the core rod of the chuck for compression (6) inserted into the tubular woven fabric (1) is a value that is calculated by subtracting "0.1 mm±0.03 mm" from the minimum inner diameter of the tubular woven fabric (1). The diameter of the hole of the receiving portion for compression (7) is equal to the minimum inner diameter of the tubular woven fabric. The "equal diameter" does not need to be exactly the same diameter, and may have a deviation of about ±0.03 mm. FIG. 3 is a schematic diagram of a device for measurement of the gauge length of the tubular woven fabric under elongation. In the device as shown in FIG. 3, HANDY DIGITAL FORCE GAUGE HF-1 (rated capacity: 10 N) made by Japan Instrumentation System Co., Ltd. is placed as a load gauge (force gauge) (4) on a platform (5). The load gauge (4) is equipped with a chuck for elongation (8). A receiving portion for elongation (9) having a core rod capable of being inserted into the tubular woven fabric (1) is placed on the platform (5). The tubular woven fabric (1) was fastened on the core rods at each of the outer sides of the gauge marks with fastening cords (10). The tubular woven fabric (1) was then elongated in the warp direction by applying a stress of 0.01 cN/dtex, and the gauge length (L2) (gauge length under elongation) was measured with a caliper. The measurement was repeated five times with different specimens, and the mean value was used for analysis. The stress was calculated by Expression (4):

$$\text{Stress (cN)}=0.01\times\text{fineness of warp yarns}\times\text{number of warp ends} \quad (4)$$

(6) Maximum Outer Diameter (a) and Minimum Outer Diameter (b) of Tubular Woven Fabric In the same manner as in the above (5), a tubular woven fabric was compressed in the warp direction by applying a stress of 0.01 cN/dtex, and the outer diameter of the tubular woven fabric was measured with a caliper. The measurement was repeated five times with different specimens, and the maximum value was taken as "the maximum outer diameter (a)". The tubular woven fabric was elongated in the warp direction by applying a stress of 0.01 cN/dtex, and the outer diameter of the tubular woven fabric was measured with a caliper. The measurement was repeated five times with different specimens, and the minimum value was taken as "the minimum outer diameter (b)". In each test, the outer diameter was measured at three locations: the center between the two gauge marks drawn on the tubular woven fabric, and 5 mm inside of each of the gauge marks. Since the measurement at each location was repeated five times with different specimens, the measurement was performed 15 times in total.

(7) Irregularity of Inner Surface of Tubular Woven Fabric

A tubular woven fabric was cut in half in the warp direction. The weftwise cross section was photographed at 150-fold magnification with an electron microscope, and the difference between the top of the warp yarn and the top of the adjacent weft yarn on the inner surface of the tubular woven fabric was determined. The measurement was repeated five times with different specimens, and the mean value was used for analysis. The mean value was taken as "the irregularity of the inner surface of a tubular woven fabric".

(8) Weave Density

The weave density was determined in accordance with JIS L 1096:2010 8.6.1. A specimen was placed on a flat table, and unnatural wrinkles and tension were removed. The number of the warp and weft yarns in a length of 0.5 cm was counted at five different locations, and the mean value was calculated and expressed as the number of the yarns per 2.54 cm.

(9) Conditions for Preparation of a Monomer Mixture Solution

The following components were mixed to prepare a monomer mixture solution for the cover:
Trifluoroethyl acrylate (Viscoat 3F; Osaka Organic Chemical Industry Ltd.), 57.9 parts by weight;
2-Ethylhexyl acrylate, 7 parts by weight;
Dimethylaminoethyl acrylate, 0.1 parts by weight;
Coloring agent (Reactive Blue 246), 0.02 parts by weight;
Polymerization initiator ("IRGACURE (registered trademark)") 819; Chiba Specialty Chemicals), 0.5 parts by weight;
t-Amyl alcohol, 10 parts by weight;
Poly(dimethyl siloxane) (FM7726; JNC Corporation; weight-average molecular weight: 29 kD; number-average molecular weight: 26 kD), 28 parts by weight;
Poly(dimethyl siloxane) (FM0721; JNC Corporation; weight-average molecular weight: 5,000), 7 parts by weight.
The above components were added, mixed well, and agitated. The mixture was filtered through a membrane filter (0.45 μm) to remove insoluble matter, and a monomer mixture solution was thereby obtained.

(10) Kink Resistance

The kink resistance was determined by measuring the kink radius of 4 to 15 mm in accordance with the guidance of ISO 7198. Briefly, a tubular structure was formed into a loop, and the diameter of the loop of the tubular structure was gradually decreased until kinking occurred. A tubular mandrel with a known radius was placed in the loop to measure the radius when the inner diameter became less than 50%. Internal pressure was not applied for the purpose of the evaluation of the genuine kink resistance of the tubular woven fabric.

(11) Amount of Functional Groups on the Surface of the Cover

Single-reflection infrared spectroscopy (ATR) was performed on the surface of the cover under the following measurement conditions:
Instrument: Varian 7000;
Light source: high luminance ceramics;
Detector: DTGS (deuterated triglycine sulphate);
Purge: nitrogen gas;
Resolution: 4 cm$^{-1}$;
Cumulative number: 128;
Measurement method: single reflection-type;
Incidence angle: 45°;
Prism: Ge;
Measuring wavelength: 2.5 to 25 μm.

By subjecting the surface of the cover to a measurement by single-reflection infrared spectroscopy (ATR) at a wavelength of 2.5 to 25 μm and an angle of incidence of 45°, the absorbance $I^1$ of 1740 to 1780 cm$^{-1}$ due to stretching vibration of C=O originated from ester groups and the absorbance $I^2$ of 1430 to 1470 cm$^{-1}$ due to bending vibration of C—H originated from alkyl groups can be determined from the obtained infrared spectrum. The ratio $I^1/I^2$ of absorbance of ester group to that of alkyl group was further calculated from the absorbance values.

(12) Water Leakiness Test

Each cylindrical structure was cut to a length of 3 cm, one end of which was connected with a connector and a silicone tube and the other end of which was closed with a clamp. RO water at 18° C. was delivered through the silicone tube using a peristaltic pump to fill the cylindrical structure with the RO water. Next, a 16-gauge SURFLO indwelling needle was used to puncture the cylindrical structure at an angle of 45°, to which a load corresponding to a water pressure of 120 mmHg was applied after withdrawal of the needle. The amount of water leaked from the cylindrical structure for one minute was weighed to calculate the water leakiness per puncture event. Subsequently, the number of puncture events was calculated by multiplying the outer surface area of the used cylindrical structure by a ratio of 8 events/outer surface area (cm$^2$) to puncture the cylindrical structure along a longitudinal axis with preventing a newly perforated hole from overlapping an already perforated hole, after which the same operation as described above was repeated to calculate the water leakiness per eight puncture events per cm$^2$.

Reference Example 1

In weaving process, the following warp yarns (warp yarn A and warp yarn B) and weft yarns (weft yarn C and weft yarn D) were used.
Warp yarn A (sea-island composite fibers): polyethylene terephthalate fiber yarn, 66 dtex, 9 filaments (after removal of the sea component: 52.8 dtex, 630 filaments)
Warp yarn B (soluble yarn): easily alkali-soluble polyester fiber yarn copolymerized with sodium 5-sulfoisophthalate, 84 dtex, 24 filaments
Weft yarn C (inner layer) (sea-island composite fibers): polyethylene terephthalate fiber yarn, 66 dtex, 9 filaments (after removal of the sea component: 52.8 dtex, 630 filaments)
Weft yarn D (outer layer): polyethylene terephthalate fiber yarn, 56 dtex, 18 filaments In the weaving process, a post-processing was performed setting the tension of the warp yarn B during weaving to 0.9 cN/dtex, and the tension of the warp yarn A during weaving to 0.1 cN/dtex. As a result, a tubular woven fabric with an inner diameter of 3 mm was woven using the above warp and weft yarns wherein the weave density after post-processing was as follows: the warp yarn A, 201 ends/inch (2.54 cm); the weft yarn C, 121 picks/inch (2.54 cm); and the weft yarn D, 121 picks/inch (2.54 cm). The warp yarn A and warp yarn B were arranged in an alternating pattern of three ends of the warp yarn A and one end of the warp yarn B. The warp yarn B was arranged between the weft yarn C arranged in the inner layer and the weft yarn D arranged in the outer layer. Post-processing was then performed in the following steps.

(a) Hot Water Washing

Hot water washing of the tubular woven fabric was performed at 98° C. for 20 minutes.

(b) Pre-Heat Setting

A round rod with an outer diameter of 2.8 mm was inserted into the tubular woven fabric. Both ends of the fabric were fastened on the rod with a wire, and the fabric was heated. The pre-heat setting was performed at 180° C. for 5 minutes. The round rod was made of stainless steel.

(c) Removal of Sea Component

The sea component of the warp yarn A and the weft yarn C of the tubular fabric was removed, and the warp yarn B was dissolved and removed.

(c-1) Acid Treatment

Maleic acid was used for acid treatment. The acid treatment of the tubular woven fabric was performed at a concentration of 0.2% by mass at 130° C. for 30 minutes.

(c-2) Alkali Treatment

Sodium hydroxide was used for alkali treatment. The alkali treatment of the tubular woven fabric was performed at a concentration of 1 wt % at 80° C. for 90 minutes.

(d) Heat Setting (First Stage)

A round rod with an outer diameter of 3 mm was inserted into the tubular woven fabric. The tubular woven fabric was compressed as much as possible in the warp direction to the extent that wrinkles did not appear. Both ends of the fabric were then fastened on the rod with a wire or another material. The fabric was then heated. The heat setting was performed at 180° C. for 5 minutes. The round rod was made of stainless steel.

(e) Heat Setting (Second Stage)

A round rod with an outer diameter of 3 mm was inserted into the tubular woven fabric. The tubular woven fabric was elongated by 30% in the warp direction, and both ends of the fabric were fastened on the rod with a wire or another material. The fabric was then heated. The heat setting was performed at 170° C. for 5 minutes. The round rod was made of stainless steel. The characteristics of the thus produced tubular woven fabric (the fineness, the filament count, the single filament diameter, the inner diameter of the cylindrical woven fabric (the maximum and the minimum), the outer diameter of the cylindrical woven fabric (the maximum and the minimum), the distance L1 between marked lines of the cylindrical woven fabric obtained when compressed, the distance L2 between marked lines obtained when elongated, the maximum outer diameter "a", the minimum outer diameter "b", the fluctuation index (C), and the inner surface roughness) are shown in Table 1. In addition, the kink radius measured by the above-described method and the result of the water leakiness test are shown in Table 2.

Reference Example 2

The tubular woven fabric of Reference Example 1 was immersed in an aqueous solution of 5.0 wt % potassium permanganate (Wako Pure Chemical Industries, Ltd.) and 0.6 mol/L sulfuric acid (Wako Pure Chemical Industries, Ltd.) at 60° C. for 3 hours to allow hydrolysis and oxidation reaction to occur. The tubular woven fabric was then immersed in an aqueous solution of 0.5 wt % DMT-MM (Wako Pure Chemical Industries, Ltd.) and 5.0 wt % PEI (LUPASOL (registered trademark) P; BASF SE) at 30° C. for 2 hours to covalently bind PEI to the inner surface of the tubular woven fabric of Reference Example 1 via condensation reaction.

The tubular woven fabric was then immersed in a 1 wt % aqueous solution of ethyl bromide (Wako Pure Chemical Industries, Ltd.) in methanol at 35° C. for 1 hour. The solution was then heated to 50° C., and the reaction was continued for 4 hours to quaternize the PEI covalently bound to the tubular woven fabric of Reference Example 1 to form a quaternary ammonium PEI.

Finally, the tubular woven fabric was immersed in an aqueous solution of 0.75 wt % heparin sodium (Organon API) and 0.1 mol/L sodium chloride (pH=4) at 70° C. for 6 hours to ionically bind heparin to the quaternary ammonium PEI. In this manner, a tubular woven fabric having an antithrombogenic property on the inner surface was produced. The total amount of heparin coated on the obtained tubular woven fabric is shown in Table 3.

Example 1

A 6-cm round bar made of stainless steel having a diameter of 3 mm was inserted into the tubular woven fabric obtained in Reference Example 1 and having a length of 5 cm, and the resulting tubular woven fabric with the inserted round bar made of stainless steel was placed into a tubular mold made of polypropylene and having a diameter of 6 mm, an inner diameter of 4.5 mm, and a length of 6 cm, and one port of the mold was sealed with a rubber stopper. The prepared monomer mixture solution was introduced into the gap between the tubular mold and the tubular woven fabric from the other port of the mold until the tubular woven fabric was completely immersed, and then polymerized by exposure to light (1.01 mW/cm$^2$; 20 minutes) using fluorescent lamps (Toshiba Corporation; F1-6D; daylight color; 6 W; four lamps). After polymerization, the tubular woven fabric was immersed in isopropanol together with the mold and heated at 80° C. for 1 hour, and the obtained tubular structure was then released from the mold together with the round bar made of stainless steel. Furthermore, the tubular structure was deprived of the round bar made of stainless steel after immersion in isopropanol at room temperature for 30 minutes, and then air-dried overnight. The results of the kink radius, water leakiness, and ratio of absorbance $I^1/I^2$ of the obtained tubular structure are shown in Table 2.

Example 2

A tubular woven fabric covered with the copolymer and obtained by the same procedures as in Example 1 was immersed in an alkali treatment solution of sodium hydroxide prepared at a concentration of 4.0 mol/L in an aqueous solution of ethanol at a concentration of 10 v/v % and left to stand at 60° C. for a reaction time of 1 hour. After the reaction, the tubular structure was withdrawn from the treatment solution, washed with RO water three times, and then air-dried overnight. The results of the kink radius, water leakiness, and ratio of absorbance $I^1/I^2$ of the obtained tubular structure are shown in Table 2.

Examples 3 to 9

The same procedures as in Example 2 were repeated, except that the concentration of sodium hydroxide in the alkali treatment solution and the reaction time were changed respectively as follows: Example 3, a concentration of sodium hydroxide of 2.0 mol/L and 1 hour of reaction time; Example 4, a concentration of sodium hydroxide of 1.0 mol/L and 6 hours of reaction time; Example 5, a concentration of sodium hydroxide of 0.5 mol/L and 6 hours of reaction time; Example 6, a concentration of sodium hydroxide of 0.25 mol/L and 6 hours of reaction time; Example 7, a concentration of sodium hydroxide of 0.125 mol/L and 6 hours of reaction time; Example 8, a concentration of sodium hydroxide of 0.05 mol/L and 6 hours of reaction time; Example 9, a concentration of sodium hydroxide of 0.01 mol/L and 6 hours of reaction time. The results of the kink radius, water leakiness, and ratio of absorbance $I^1/I^2$ of each of the obtained tubular structures are shown in Table 2.

Comparative Example 1

The tubular woven fabric obtained by the same procedures as in Reference Example 1 and having a length of 5 cm was evenly coated with a one-component curable silicone (RTV rubber for general industrial purposes; KE42T-330; manufactured by Shin-Etsu Chemical Co., Ltd.) and then air-dried for 3 days. Thus, a tubular structure in which a base composed of only polyester was covered with a cover composed of only silicone was obtained. The results of the kink radius and water leakiness of the obtained tubular structure are shown in Table 2.

Comparative Example 2

The tubular woven fabric obtained by the same procedures as in Reference Example 1 and having a length of 5 cm was wrapped in five layers of a dressing tape made of only polyurethane and having a film thickness of 20 μm (waterproof film roll; manufactured by Kyowa Ltd.). Thus, a tubular structure in which a base composed of only polyester was covered using a urethane tape as a cover was obtained. The results of the kink radius and water leakiness of the obtained tubular structure are shown in Table 2.

Comparative Example 3

The tubular woven fabric obtained by the same procedures as in Reference Example 1 and having a length of 5 cm was coated with a bioabsorbable material, namely a solution of gelatin (BEMATRIX (registered trademark) Gelatin LS-H; manufactured by Nitta Gelatin Inc.) prepared at a concentration of 30 wt %, and then cooled at 4° C. for 1 hour to solidify the gelatin solution. Then, the tubular woven fabric was immersed in 0.2% glutaraldehyde solution for 30 minutes to cross-link the solidified gelatin gel, and then dried at 40° C. overnight. Thus, a tubular structure in which a base composed of only polyester was covered with a cross-linked gelatin gel as a cover was obtained. The results of the kink radius and water leakiness of the obtained tubular structure are shown in Table 2.

Comparative Example 4

An artificial blood vessel composed of only ePTFE and having a length of 5 cm, an inner diameter of 3 mm, and a thickness of 0.5 mm (GORE-TEX (registered trademark); manufactured by W.L. Gore & Associates, Inc.) was provided and used as Comparative Example 4. The results in the kink radius and water leakiness are shown in Table 2.

Example 10

An artificial blood vessel composed of only ePTFE provided in Comparative Example 4 was used as a base and covered by a copolymer by the same procedures as in Example 1. The results of the kink radius and water leakiness of the obtained tubular structure are shown in Table 2.

Comparative Example 5

An artificial blood vessel composed of only ePTFE provided in Comparative Example 4 was used as a base and covered with silicone by the same procedures as in Comparative Example 1 to obtain a tubular structure comprising an ePTFE base covered with silicone, which was used for the following tests as Comparative Example 5. The results of the kink radius and water leakiness of the obtained tubular structure are shown in Table 2.

Comparative Example 6

An artificial blood vessel composed of only ePTFE provided in Comparative Example 4 was used as a base and wrapped with a dressing tape made of urethane by the same procedures as in Comparative Example 2 to obtain a tubular structure comprising an ePTFE base covered with a urethane tape, which was used for the following test as Comparative Example 6. The results of the kink radius and water leakiness of the obtained tubular structure are shown in Table 2.

Comparative Example 7

An artificial blood vessel composed of only polyurethane and having a length of 5 cm, an inner diameter of 6 mm, and a thickness of 1.0 mm (THORATEC (registered trademark); manufactured by Goodman Co., Ltd.) was provided and used for the following tests as Comparative Example 7. The results of the kink radius and water leakiness are shown in Table 2.

Comparative Example 8

An artificial blood vessel having a trilayer structure composed of polyester, styrene elastomer, and polyolefin, respectively, and having a length of 5 cm, an inner diameter of 5.6 mm, and a thickness of 1.2 mm (GRASIL (registered trademark); manufactured by Terumo Corporation) was provided and used for the following tests as Comparative Example 8. The results of the kink radius and water leakiness are shown in Table 2.

TABLE 1

|  |  | Reference Example 1 |
|---|---|---|
| Yarn type of warp yarn A | — | polyethylene terephthalate |
| Fineness of warp yarn A | dtex | 52.8 |
| Filament count of warp yarn A | filaments | 630 |
| Single filament diameter of warp yarn A | μmφ | 2.78 |
| Yarn type of weft yarn C | — | polyethylene terephthalate |
| Fineness of weft yarn C | dtex | 52.8 |
| Filament count of weft yarn C | filaments | 630 |
| Single filament diameter of weft yarn C | μmφ | 2.78 |
| Yarn type of weft yarn D | — | polyethylene terephthalate |
| Fineness of weft yarn D | dtex | 56 |
| Filament count of weft yarn D | filaments | 18 |
| Single filament diameter of weft yarn D | μmφ | 16.94 |
| Yarn type of warp yarn E | — | — |
| Fineness of warp yarn E | dtex | — |
| Filament count of warp yarn E | filaments | — |
| Single filament diameter of warp yarn E | μmφ | — |
| Yarn type of weft yarn F | — | — |
| Fineness of weft yarn F | dtex | — |
| Filament count of weft yarn F | filaments | — |
| Single filament diameter of weft yarn F | μmφ | — |
| Maximum inner diameter of woven fabric | mmφ | 3.05 |
| Minimum inner diameter of woven fabric | mmφ | 3.02 |
| Maximum outer diameter of woven fabric | mmφ | 3.76 |
| Minimum outer diameter of woven fabric | mmφ | 3.74 |
| Difference in outer diameter | % | 0.53 |
| Gauge length | mm | 18.8 |
| Gauge length obtained when compressed (L1) | mm | 16.5 |
| Gauge length obtained when elongated (L2) | mm | 20.5 |
| (L2 − L1)/L1 | — | 0.24 |
| Maximum outer diameter obtained when compressed (a) | mmφ | 3.96 |
| Minimum outer diameter obtained when elongated (b) | mmφ | 3.69 |
| Change index (c) | — | 0.07 |
| Inner surface roughness of tubular woven fabric μmφ |  | 52 |

TABLE 2

| Example Number | Concentration of sodium hydroxide (mol/L) | Treatment time (hours) | $I^1/I^2$ | Kink radius (mm) | Water leakiness (g/min) per puncture event | per eight puncture events per cm² |
|---|---|---|---|---|---|---|
| Reference Example 1 | — | — | — | <4.0 | 181.59 | 194.69 |
| Example 1 | — | — | 4.40 | 4.5 | 10.53 | 169.40 |
| Example 2 | 4.0 | 1 | 1.39 | 4.5 | 0.83 | 0 |
| Example 3 | 2.0 | 1 | 1.66 | 4.5 | 0 | 0.41 |
| Example 4 | 1.0 | 6 | 2.39 | 4.5 | 0.98 | 3.92 |
| Example 5 | 0.5 | 6 | 2.88 | 4.5 | 3.13 | 6.46 |
| Example 6 | 0.25 | 6 | 3.09 | 4.5 | 0 | 5.00 |
| Example 7 | 0.125 | 6 | 3.31 | 4.5 | 0.68 | 4.59 |
| Example 8 | 0.05 | 6 | 3.33 | 4.5 | 8.48 | 88.45 |
| Example 9 | 0.01 | 6 | 3.48 | 4.5 | 0.40 | 157.27 |
| Example 10 | — | — | — | 4.5 | 11.58 | 155.60 |
| Comparative Example 1 | — | — | — | 6.0 | 31.15 | 286.70 |
| Comparative Example 2 | — | — | — | 15 | 1.65 | 80.90 |
| Comparative Example 3 | — | — | — | <4.0 | 122.45 | 233.62 |
| Comparative Example 4 | — | — | — | <4.0 | 108.47 | 274.97 |
| Comparative Example 5 | — | — | — | <4.0 | 98.38 | 245.67 |
| Comparative Example 6 | — | — | — | 6.0 | 50.46 | 192.78 |

TABLE 2-continued

| Example Number | Concentration of sodium hydroxide (mol/L) | Treatment time (hours) | $I^1/I^2$ | Kink radius (mm) | Water leakiness (g/min) per puncture event | Water leakiness (g/min) per eight puncture events per cm² |
|---|---|---|---|---|---|---|
| Comparative Example 7 | — | — | — | 12.0 | 1.88 | 119.26 |
| Comparative Example 8 | — | — | — | 14.5 | 6.09 | 121.11 |

TABLE 3

| | Total coating amount of heparin (mIU/mg) |
|---|---|
| Reference Example 2 | 1100 |

INDUSTRIAL APPLICABILITY

The above-described tubular structure can usefully be used for, for example, hoses for transporting liquids and powders and for protecting linear materials, and for bases for tubular filters and artificial blood vessels. The above-described tubular structure can be suitably used as a medical tube implantable in the body and is suitable for artificial blood vessels because of the presence of kink resistance, and can also be particularly suitably used for dialysis shunts because of the reduced water leakiness after getting pierced, which shunts need to be pierced repeatedly.

The invention claimed is:

1. A tubular structure comprising a tubular base and a cover covering said base, wherein
said cover comprises a copolymer containing a silicone monomer and a polymerizable monomer having a fluoroalkyl group(s) as monomer units,
wherein said base is composed of a polyester, polyurethane, or polytetrafluoroethylene.

2. The tubular structure of claim 1, wherein said silicone monomer is represented by Formula (I):

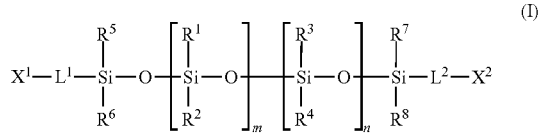

(I)

wherein $X^1$ and $X^2$ independently represent a polymerizable functional group; $R^1$ to $R^8$ independently represent hydrogen or a functional group selected from the group consisting of $C_1$-$C_{20}$ alkyl groups, phenyl group, and $C_1$-$C_{20}$ fluoroalkyl groups; $L^1$ and $L^2$ independently represent a divalent group; and m and n independently represent an integer of 0 to 1500 with the proviso that m and n are not simultaneously 0.

3. The tubular structure of claim 2, wherein said $X^1$ and $X^2$ are (meth)acryloyl groups.

4. The tubular structure of claim 3, wherein said polymerizable monomer having a fluoroalkyl group(s) is represented by Formula (II):

(II)

wherein $R^9$ represents hydrogen or a methyl group; and $R^{10}$ represents a $C_1$-$C_{20}$ fluoroalkyl group.

5. The tubular structure of claim 3, which satisfies Expression (1):

$$I^1/I^2 \leq 5.0 \quad (1)$$

wherein $I^1$ represents an absorbance of 1740 to 1780 cm$^{-1}$ due to stretching vibration of C═O originated from ester groups; and $I^2$ represents an absorbance of 1430 to 1470 cm$^{-1}$ due to bending vibration of C—H originated from alkyl groups,
when the surface of said cover is subjected to a measurement by single-reflection infrared spectroscopy at a wavelength of 2.5 to 25 μm and an angle of incidence of 45°.

6. The tubular structure of claim 3, wherein said copolymer has a carboxyl group(s) and/or a hydroxyl group(s).

7. The tubular structure of claim 2, wherein said polymerizable monomer having a fluoroalkyl group(s) is represented by Formula (II):

(II)

wherein $R^9$ represents hydrogen or a methyl group; and $R^{10}$ represents a $C_1$-$C_{20}$ fluoroalkyl group.

8. The tubular structure of claim 2, which satisfies Expression (1):

$$I^1/I^2 \leq 5.0 \quad (1)$$

wherein $I^1$ represents an absorbance of 1740 to 1780 cm$^{-1}$ due to stretching vibration of C═O originated from ester groups; and $I^2$ represents an absorbance of 1430 to 1470 cm$^{-1}$ due to bending vibration of C—H originated from alkyl groups,
when the surface of said cover is subjected to a measurement by single-reflection infrared spectroscopy at a wavelength of 2.5 to 25 μm and an angle of incidence of 45°.

9. The tubular structure of claim 2, wherein said copolymer has a carboxyl group(s) and/or a hydroxyl group(s).

10. The tubular structure of claim 1, wherein said polymerizable monomer having a fluoroalkyl group(s) is represented by Formula (II):

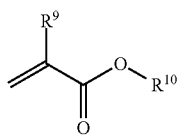
(II)

wherein $R^9$ represents hydrogen or a methyl group; and $R^{10}$ represents a $C_1$-$C_{20}$ fluoroalkyl group.

11. The tubular structure of claim 10, which satisfies Expression (1):

$$I^1/I^2 \leq 5.0 \tag{1}$$

wherein $I^1$ represents an absorbance of 1740 to 1780 cm$^{-1}$ due to stretching vibration of C=O originated from ester groups; and $I^2$ represents an absorbance of 1430 to 1470 cm$^{-1}$ due to bending vibration of C—H originated from alkyl groups,
when the surface of said cover is subjected to a measurement by single-reflection infrared spectroscopy at a wavelength of 2.5 to 25 μm and an angle of incidence of 45°.

12. The tubular structure of claim 10, wherein said copolymer has a carboxyl group(s) and/or a hydroxyl group(s).

13. The tubular structure of claim 1, which satisfies Expression (1)

$$I^1/I^2 \leq 5.0 \tag{1}$$

wherein $I^1$ represents an absorbance of 1740 to 1780 cm$^{-1}$ due to stretching vibration of C=O originated from ester groups; and $I^2$ represents an absorbance of 1430 to 1470 cm$^{-1}$ due to bending vibration of C—H originated from alkyl groups,
when the surface of said cover is subjected to a measurement by single-reflection infrared spectroscopy at a wavelength of 2.5 to 25 μm and an angle of incidence of 45°.

14. The tubular structure of claim 13, wherein said copolymer comprises a structure represented by Formula (III):

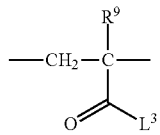
(III)

wherein $R^9$ represents hydrogen or a methyl group, and $L^3$ represents a monovalent group.

15. The tubular structure of claim 1, wherein said copolymer has a carboxyl group(s) and/or a hydroxyl group(s).

16. The tubular structure of claim 1, wherein said tubular base is a tubular woven fabric comprising warp yarns and weft yarns, said tubular structure having an outer diameter with a variation of within 10% along the warp direction and satisfying Expression (2):

$$(L^2-L^1)/L1 \geq 0.1 \tag{2}$$

wherein L1 is a gauge length of the tubular woven fabric when compressed in the warp direction by applying a stress of 0.01 cN/dtex, as determined after the outer diameter of the tubular woven fabric is measured without applying stress to the tubular woven fabric to determine a maximum outer diameter and then gauge marks are drawn around an outer circumference of the tubular woven fabric so that the gauge marks are separated by a length of five times the maximum outer diameter of the tubular woven fabric; and L2 is a gauge length when elongated in a warp direction by applying a stress of 0.01 cN/dtex.

17. The tubular structure of claim 1, wherein said tubular base is a tubular woven fabric comprising warp yarns and weft yarns, wherein said tubular woven fabric satisfies Expression (3):

$$0.03 \leq (a-b)/a < 0.2 \tag{3}$$

wherein "a" is a maximum outer diameter of the tubular woven fabric when compressed in a warp direction by applying a stress of 0.01 cN/dtex, and "b" is a minimum outer diameter of the tubular woven fabric when elongated in the warp direction by applying a stress of 0.01 cN/dtex.

18. The tubular structure of claim 1, which is a medical tube implantable in the body.

19. The tubular structure of claim 1, which is an artificial blood vessel.

* * * * *